United States Patent [19]
Baerveldt

[11] Patent Number: 6,050,970
[45] Date of Patent: Apr. 18, 2000

[54] METHOD AND APPARATUS FOR INSERTING A GLAUCOMA IMPLANT IN AN ANTERIOR AND POSTERIOR SEGMENT OF THE EYE

[75] Inventor: George Baerveldt, Shaker Heights, Ohio

[73] Assignee: Pharmacia & Upjohn Company, Irvine, Calif.

[21] Appl. No.: 08/853,076

[22] Filed: May 8, 1997

[51] Int. Cl.[7] ................................................ A61M 5/00
[52] U.S. Cl. ........................... 604/28; 604/8; 604/10
[58] Field of Search ..................................... 604/8–10, 46, 604/294, 28, 30, 128, 131, 149, 280; 606/108, 109; 623/4

[56] References Cited

U.S. PATENT DOCUMENTS 2,969,066  1/1961  Holter et al. .
3,109,429  11/1963  Schwartz .

(List continued on next page.)

FOREIGN PATENT DOCUMENTS

| 0102747 | 3/1984 | European Pat. Off. . |
| 0168201 | 1/1986 | European Pat. Off. . |
| 2233028 | 6/1973 | France . |
| 906561 | 2/1982 | U.S.S.R. . |
| 2101891 | 1/1983 | United Kingdom . |
| 2160778 | 1/1986 | United Kingdom . |
| 2187963 | 9/1987 | United Kingdom . |

OTHER PUBLICATIONS

Krupin, et al., "Filtering Valve Implant Surgery for Eyes with Neovascular Glaucoma." *American Journal of Ophthalmology*, vol. 89, No. 3, 1980, pp. 338–343.

Lee, et al., "Aqueous–Venous Shunt for Glaucoma," *Arch Ophthalmol*, vol. 99, Nov. 1981, pp. 2007–2012.

Molteno, "Use of Molteno Implants to Treat Secondary Glaucoma," *Glaucoma*, Grune & Stratton, Ltd., 1986, pp. 211–238.

Bickford, "Molteno Implant System, for Patient with Previously Unsuccessful Glaucoms Surgery," *Journal of Ophthalmic Nursing & Technology*, vol. 6, No. 6, 1987, pp. 224–229.

Minckler, et al., "Clinical Experience with the Single–plate Molteno Implant in Complicated Glaucomas," *Ophthalmology*, vol. 95, No. 9, Sep. 1988, pp. 1181–1188.

"Experience with Molteno–type shunts . . . ," *Ocular Surgery News*, Jun. 1, 1989, pp. 27–29.

Davidovski, et al., "Long–Term Results with the White Glaucoma Pump–Stunt," *Ophthalmic Surgery*, vol. 21, No. 4 1990, pp. 288–293.

White, "A New Implantable Ocular Pressure Relief Device," University of South Dakota Medical School, Sioux Falls, San Diego, one page.

"Molteno Seton Implant, for Management of Refractory Glaucoma," Staar Surgical Company, Monrovia, California, one page brochure.

"Intraocular Pressure," *Alder's Physiology of the Eye*, Chapter 5, pp. 249–277.

*Primary Examiner*—Ronald Stright
*Assistant Examiner*—David J. Cho
*Attorney, Agent, or Firm*—Knobbe, Martens, Olson & Bear, LLP

[57] ABSTRACT

A method of treating glaucoma in an eye utilizing an implant is disclosed. The implant comprises an elastomeric plate having first and second surfaces and an non-valved elastomeric drainage tube. The plate is positioned over a sclera of said eye beneath Tenon's capsule, such that a portion of the plate extends into the anterior segment of the eye. The first end of said elastomeric drainage tube is open to said second surface of said plate. The second end of said drainage tube is tunneled through the sclera and cornea and inserted into the anterior chamber of said eye. Fluid communication is provided between said anterior chamber and a scar tissue bleb which forms around said implant. Preferably, a portion of the scar tissue bleb extends into the anterior segment of the eye and a portion of the scar tissue bleb extends into the posterior segment of the eye.

21 Claims, 15 Drawing Sheets

U.S. PATENT DOCUMENTS

| | | |
|---|---|---|
| 3,159,161 | 12/1964 | Ness . |
| 3,527,226 | 9/1970 | Hakim . |
| 3,788,327 | 1/1974 | Donowitz et al. . |
| 3,860,008 | 1/1975 | Miner et al. . |
| 3,915,172 | 10/1975 | Wichterle et al. . |
| 4,030,480 | 6/1977 | Meyer . |
| 4,240,434 | 12/1980 | Newkirk . |
| 4,298,994 | 11/1981 | Clayman . |
| 4,373,218 | 2/1983 | Schachar . |
| 4,402,681 | 9/1983 | Haas et al. . |
| 4,428,746 | 1/1984 | Mendez . |
| 4,457,757 | 7/1984 | Molteno . |
| 4,521,210 | 6/1985 | Wong . |
| 4,722,724 | 2/1988 | Schocket . |
| 4,729,761 | 3/1988 | White . |
| 4,863,457 | 9/1989 | Lee . |
| 4,886,488 | 12/1989 | White . |
| 4,902,292 | 2/1990 | Joseph . |
| 4,915,684 | 4/1990 | MacKeen et al. . |
| 4,936,825 | 6/1990 | Ungerleider . |
| 4,946,436 | 8/1990 | Smith . |
| 4,968,296 | 11/1990 | Ritch et al. . |
| 5,092,837 | 3/1992 | Ritch et al. ................................. 604/8 |
| 5,300,020 | 4/1994 | L'Esperance, Jr. . |
| 5,397,300 | 3/1995 | Baerveldt et al. ......................... 604/8 |
| 5,476,445 | 12/1995 | Baerveldt et al. ......................... 604/8 |
| 5,558,629 | 9/1996 | Baerveldt et al. ......................... 604/9 |
| 5,704,907 | 1/1998 | Nordquist et al. ......................... 604/8 |
| 5,725,493 | 3/1998 | Avery et al. ................................ 604/9 |

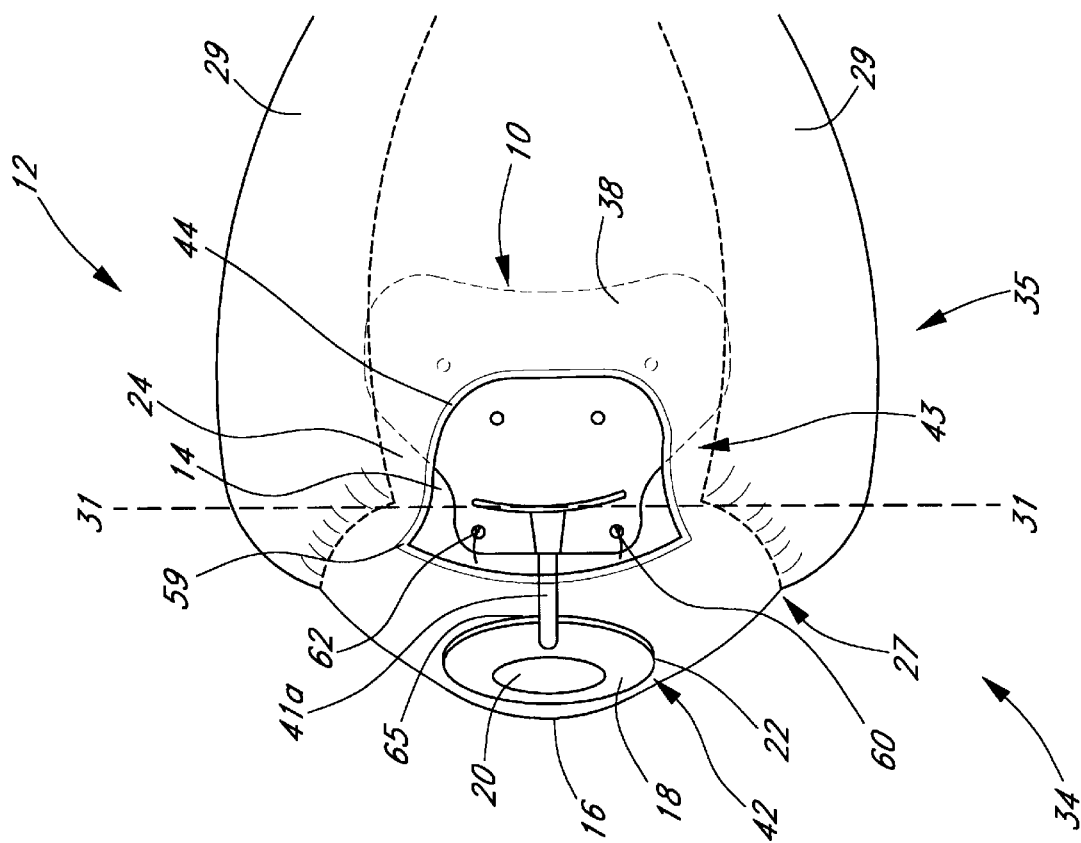

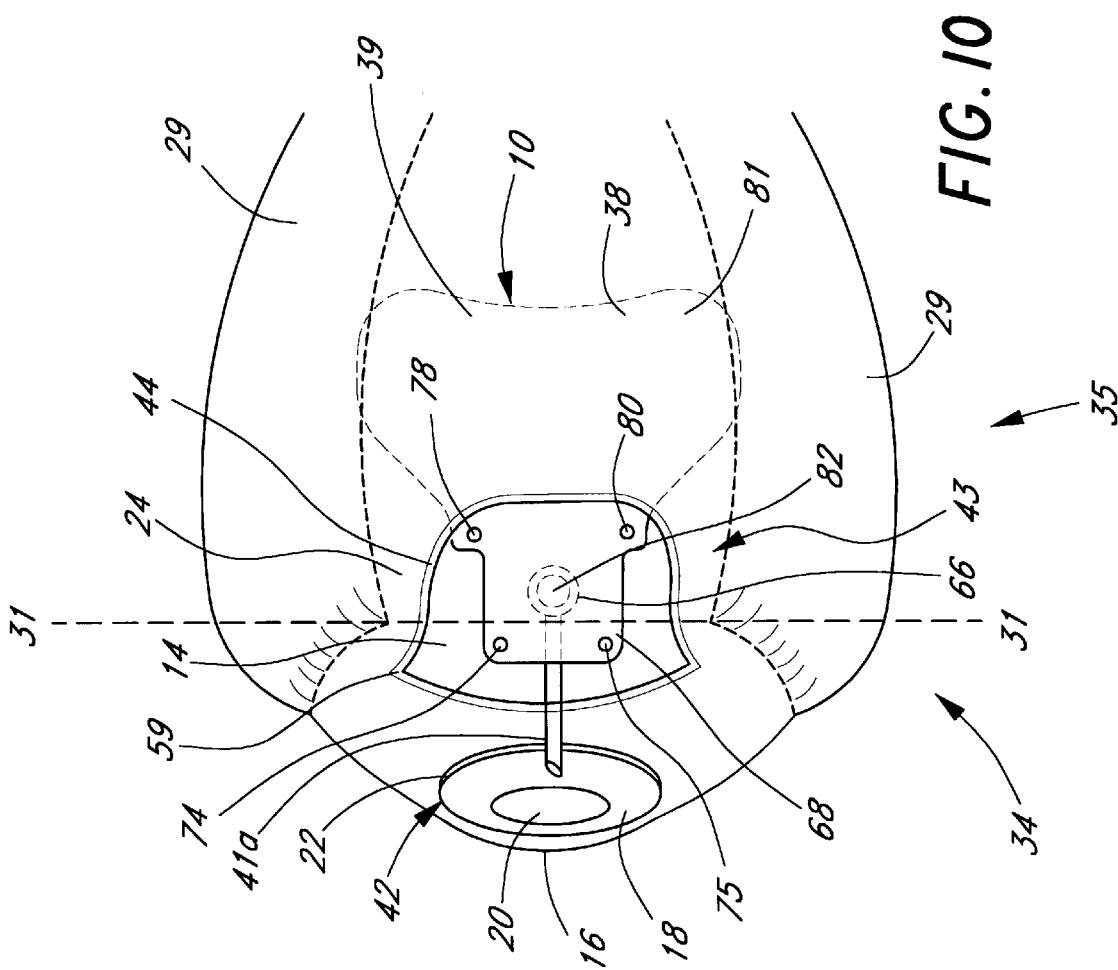

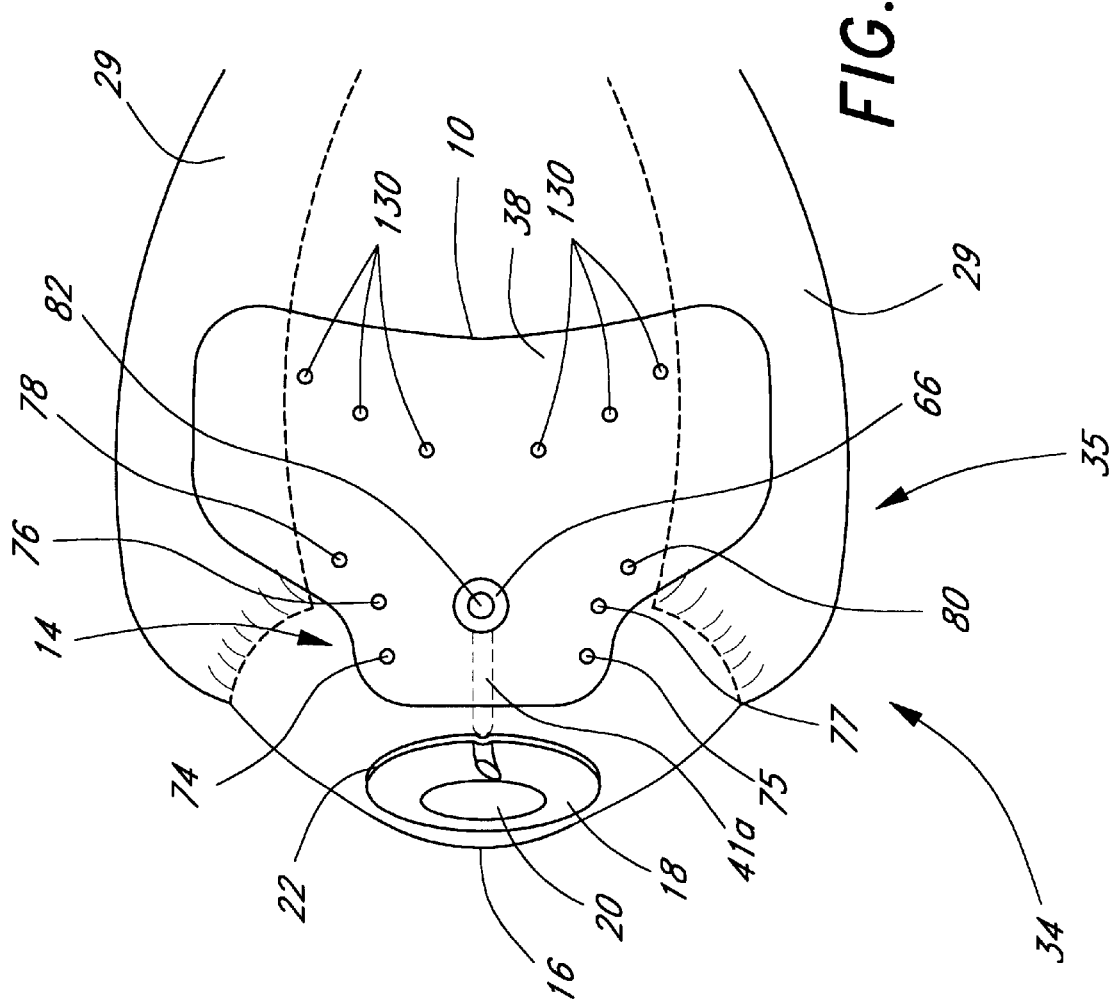

METHOD AND APPARATUS FOR INSERTING A GLAUCOMA IMPLANT IN AN ANTERIOR AND POSTERIOR SEGMENT OF THE EYE

BACKGROUND OF THE INVENTION

1. Field of the Invention

The invention relates to ocular implants, and, in particular, to an implant and method used in the treatment of glaucoma.

2. Background

Intraocular pressure in the eye is maintained by the formation and drainage of aqueous, a clear, colorless fluid that fills the anterior and posterior chambers of the eye. Aqueous normally flows from the anterior chamber of the eye out through an aqueous outflow channel at a rate of 2 to 5 microliters per minute. Glaucoma is a progressive disease of the eye characterized by a gradual increase of intraocular pressure. This increase in pressure is most commonly caused by stenosis or blockage of the aqueous outflow channel, resulting in excessive buildup of aqueous fluid in the eyeball, Other causes include increase in venous pressure outside the eye which is reflected back through the aqueous drainage channels and increased production of aqueous. In a "normal" eye, intraocular pressure ranges from 8 to 21 mm mercury. In an eye with glaucoma, this pressure can range between the so called normal pressures and pressures up to as much as 50 mm mercury. This increase in intraocular pressure produces gradual and permanent loss of vision in the afflicted eye.

Existing corrective methods for the treatment of glaucoma include drugs, surgery, and implants. Pharmacological treatment is prohibitively expensive to a large majority of glaucoma patients. In addition, many people afflicted with the disease live in remote or undeveloped remote areas where the drugs are not readily accessible. The drugs used in the treatment, in particular steroids, often have undesirable side effects and many of the long-term effects resulting from prolonged use are not yet known.

Surgical procedures have been developed in an effort to treat victims of glaucoma. An iridectomy, removal of a portion of the iris, is often used in angle-closure glaucoma wherein there is an occlusion of the trabecular meshwork by iris contact. Removal of a piece of the iris then gives the aqueous free passage from the posterior to the anterior chambers in the eye. A trabeculectomy, opening the inner wall of Schlemm's canal is often performed in cases of developmental or juvenile glaucoma so as to increase the outflow of the aqueous, thereby decreasing intraocular pressure. In adults, a trabeculotomy shunts fluid through a trap-door flap in the eye that performs a valve-like function for the first few weeks after surgery. While often successful, these surgical techniques possess inherent risks associated with invasive surgery on an already afflicted eye. Furthermore, the tissue of the eye can scar over this small area and the eye reverts to the pre-operative condition, thereby necessitating the need for further treatment.

Ocular implants are often used in long-term glaucoma treatment. One early implant was invented by Dr. Anthony Molteno and is described in the paper entitled "Use of Molteno Implants to Treat Secondary Glaucoma" by A. C. B. Molteno and published by Grune & Stratton, Ltd, 1986, pp 211–238, which is hereby incorporated by reference in its entirety. The implant was a small circular plate with a rigid translimbal drainage tube attached thereto. The plate was 8.5 mm in diameter and formed a surface area of 48 mm$^2$. This early Molteno implant was sutured to the sclera in the anterior segment of the eye at the limbus and the drainage tube was inserted into the anterior chamber of the eye. Once implanted, the body forms scar tissue around this plate. Increased pressure causes the tissues above the plate to lift and form a bleb into which aqueous flows from the anterior chamber via the drainage tube. Many problems occurred with the early Molteno device. The bleb that formed around the plate, even through it was small in surface area on the sclera, formed a very tall bleb which resulted in Dellen formation (sterile corneal ulcers). The implant had to be removed in another surgery to cure the ulcers. Further, as indicated at page 220 of Dr. Molteno's paper, his early device did not reduce the intraocular pressure enough to treat the glaucoma without the use of additional medications. Dr. Molteno redesigned his implant for insertion into the posterior segment of the eye to avoid the problems with his early anterior device.

The redesigned Molteno implant is disclosed in U.S. Pat. No. 4,457,757 entitled "Device for Draining Aqueous Humor," which is hereby incorporated by reference in its entirety. This implant is commercially available as the Molteno™ Seton Implant and also referred to as the long tube molteno implant. As indicated at page 221 of Dr. Molteno's paper, the long tube Molteno implant has been used exclusively by Dr. Molteno since 1973. The implant comprises a flexible drainage tube connected to one or more rigid plate reservoirs. The plates are shaped to conform to the curvature of the eye. The long tube Molteno implant is disadvantageous as the plates are formed of a rigid plastic which makes insertion beneath the eye tissue difficult and time-consuming. The plates are 13 mm in diameter and therefore the bleb formation area is at least 134 mm$^2$. The reservoir plate is placed under Tenon's capsule in the posterior segment of the eye and sutured to the sclera. The drainage tube is implanted into the anterior chamber through a scleral flap. A second plate can be passed under or over the superior rectus muscle also in the posterior segment of the eye and sutured to the sclera. In the redesign of the Molteno implant, Dr. Molteno not only moved the bleb forming part, or plate, of the implant back to the posterior segment of the eye, he also increased the bleb formation area from at least 48 to at least 134 mm$^2$, because it was believed that there was not enough room to form a large bleb in the anterior segment of the eye.

U.S. Pat. No. 4,750,901 issued to Molteno, which is hereby incorporated herein by reference, discloses another glaucoma implant with an elevated peripheral ridge, a subsidiary elevated ridge on the upper surface of the implant and a drainage tube which leads from the upper surface of the plate to the anterior chamber of the eye. This device is also implanted in the posterior segment of the eye under Tenon's tissue, i.e., Tenon's capsule. This Molteno patent discloses that the tube enters the peripheral ridge to a position above the upper surface of the plate and the subsidiary ridge is located around the entrance of the tube. The subsidiary ridge is forced against Tenon's capsule, to create an initial bleb cavity much smaller in area than the total bleb cavity, but both cavities are formed in the posterior segment of the eye. This Molteno patent discloses that the addition of the subsidiary ridge to the upper surface of the plate around the exit of the tube has the effect of providing a pressure sensitive one-way valve effect. The Molteno patent also discloses that, once the eye recovers from the operation, the increased production of aqueous fluid by the eye raises the pressure in the eye and also within the small bleb cavity causing the overlying Tenon's capsule to be lifted slightly, thereby allowing fluid to flow into the entire bleb cavity. In practice however, the Molteno device fails to provide an effective sealing surface with Tenon's capsule and the desired one-way valve effect does not occur.

UK Patent Application 2,160,778 entitled "Aqueous humor drainage device" discloses a similar type of implant device comprising a drainage tube and a drainage body. The tube is fixed to and opens directly onto a surface of the body. The device is sutured to the selera of the eye in the posterior segment of the eye and the tube positioned within the anterior chamber to provide outflow for the aqueous contained therein.

U.S. Pat. No. 4,729,761 discloses a Glaucoma implant with a plate, a separate fluid reservoir, a first tube between the plate and the fluid reservoir and a second tube between the fluid reservoir and the anterior chamber of the eye. The plate is attached to the sclera in the posterior segment of the eye, and a bleb forms around the plate. Despite the more anterior location of the fluid reservoir, the housing around which the bleb is formed is located in the posterior segment of the eye.

Another glaucoma implant device called the Optimed Glaucoma Implant made by Optimed, Inc. of Santa Barbara, Calif. This implant comprises a box valve connected to a drainage tube which extends into the anterior chamber of the eye. The box valve has a dimension of approximately 3 mm×2 mm×2 mm and has a maximum top surface area of 18 mm². The box has a small extension with holes therein to form suture locations to attach the box to the eye. The box contains approximately 180–200 microtubules which are attached to one end of the drainage tube. The microtubules act like a valve to limit the flow of aqueous humor from the anterior chamber. The drainage tube is implanted into the anterior chamber of the eye. The box and housing is sutured to the sclera in the anterior segment close to the limbus. The housing does not constitute a plate or a drainage surface.

SUMMARY OF THE INVENTION

The present invention provides an implant for the treatment of glaucoma having a bleb formation device and a draining tube, wherein at least a portion of the bleb formation device can be implanted in the anterior segment of the eye, thereby causing a portion of the scar tissue bleb to be formed in the anterior segment of the eye. The remainder of the bleb is formed in the posterior segment of the eye.

In one embodiment, the implant creates a temporary seal to restrict the flow of fluid from the anterior chamber of the eye and after a period of time provides flow between the larger surface around the implant and the anterior chamber of the eye. The implant comprises a single plate formed of a pliable, elastomeric material having a non-valved tube attached to and opening onto a surface of the plate. The plate is sutured to the scleral tissue in the anterior segment of the eye at the forward portion of the plate utilizing permanent sutures to keep the plate from migrating and impinging on the eye socket tissue or extruding from the eye tissue. The plate is covered by a thick flap of Tenon's capsule so that it is encapsulated within and forms a drainage bleb. The attached tube is tunneled through the sclera and the cornea and positioned within the anterior chamber to provide a drain for aqueous fluid. Because of the pliable construction, the device can be implanted with greater ease than previous implants. This substantially shortens the time required to perform the surgical procedure and to implant such large surface area implants.

In one embodiment of the present invention, the method of treating glaucoma in an eye is performed utilizing an implant. The implant comprises a bleb formation device and an elastomeric drainage tube, wherein a first end of the elastomeric drainage tube is open to a surface of the bleb formation device. The bleb formation device is positioned in the eye. A scar tissue bleb forms around the bleb formation device, such that at least a portion of the bleb is formed in the anterior segment of the eye. The second end of the drainage tube is positioned within the anterior chamber of the eye thus providing fluid communication between the anterior chamber and the scar tissue bleb. Preferably, the bleb formation device is positioned over the sclera and/or beneath Tenon's capsule of the eye.

In another embodiment of the method of treating glaucoma utilizing an implant, wherein the implant comprises a bleb formation device and an elastomeric drainage tube, the bleb formation device is positioned in the eye, such that at least a portion of the bleb formation device is anterior to the muscle insertions of the eye. The second end of the drainage tube is positioned within the anterior chamber of the eye, and fluid communication is provided between the anterior chamber and a scar tissue bleb which forms around the implant. Preferably, the bleb formation device is positioned over the sclera and/or beneath Tenon's capsule of the eye. Preferably, the bleb formation device is an elastomeric plate, wherein the first end of the tube is open to a surface of the elastomeric plate. The bleb formation device may be sutured to the eye and more preferably to the sclera of the eye. In a preferred embodiment, the bleb formation device is positioned such that between 5% and 100% of the bleb formation device is anterior to the muscle insertions of the eye. More preferably, the bleb formation device is positioned such that between 5% and 15% of the bleb formation device is anterior to the muscle insertions of the eye.

In a preferred embodiment, the implant for draining aqueous fluid from a first region of an eye to a second region of the eye which includes the sclera comprises an elastomeric plate and a drainage tube. Preferably, the first region of the eye is an anterior chamber of the eye. The elastomeric plate has first and second surfaces to conform to the second region of the eye. The drainage tube comprises a first end and a second end. The drainage tube is attached to the plate such that the first end of the drainage tube opens onto the second surface of the elastomeric plate. The second end of the drainage tube is in communication with the first region of the eye. Preferably, the drainage tube is less than 10 mm in length. More preferably, the drainage tube is less than 8 mm in length.

BRIEF DESCRIPTION OF THE DRAWINGS

FIG. 5 is a cut-away view which illustrates the implant of FIGS. 3a–3b implanted in a human eye, such that a portion of the plate of the implant extends into the anterior segment of the eye;

FIG. 7b is a cross-sectional view taken along the line 7b—7b of FIG. 7a;

FIG. 10 is a cut-away view which illustrates the implant of FIG. 6 and FIGS. 7a–7b implanted in accordance with the present invention in a human eye, such that a portion of the plate of the implant extends into the anterior segment of the eye;

FIG. 11 is a cut-away view which illustrates an implant similar to the implant of FIG. 6, but with a larger surface area implanted in a human eye, such that a portion of the plate of the implant extends into the anterior segment of the eye;

DETAILED DESCRIPTION OF THE INVENTION

Figure 1:
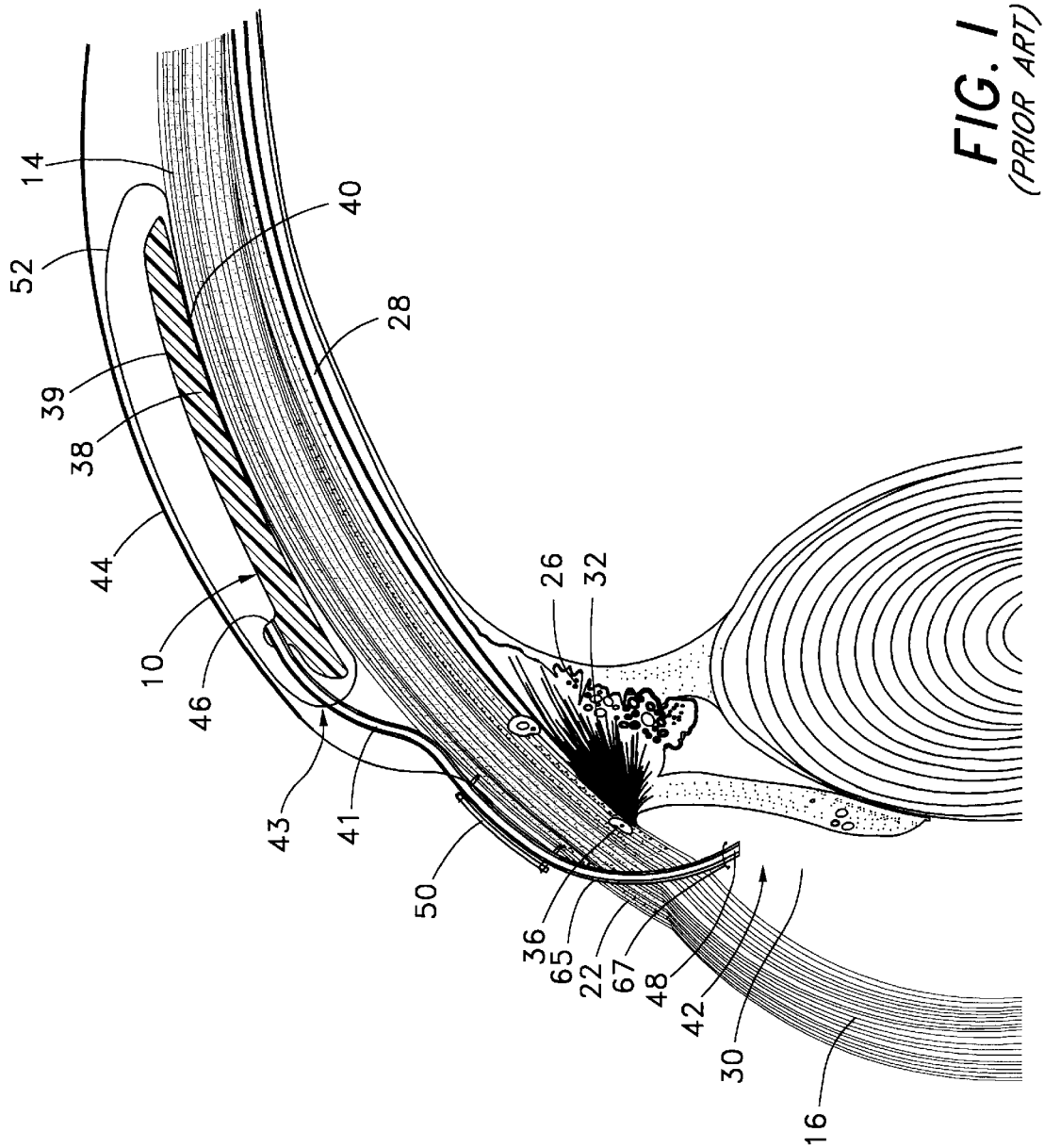
FIG. 1 and FIG. 2 are, respectively, a cross section and cut-away view which illustrate a prior art implant in a human eye, such that the entire plate of the implant is in the posterior segment of the eye.
Figure 2:
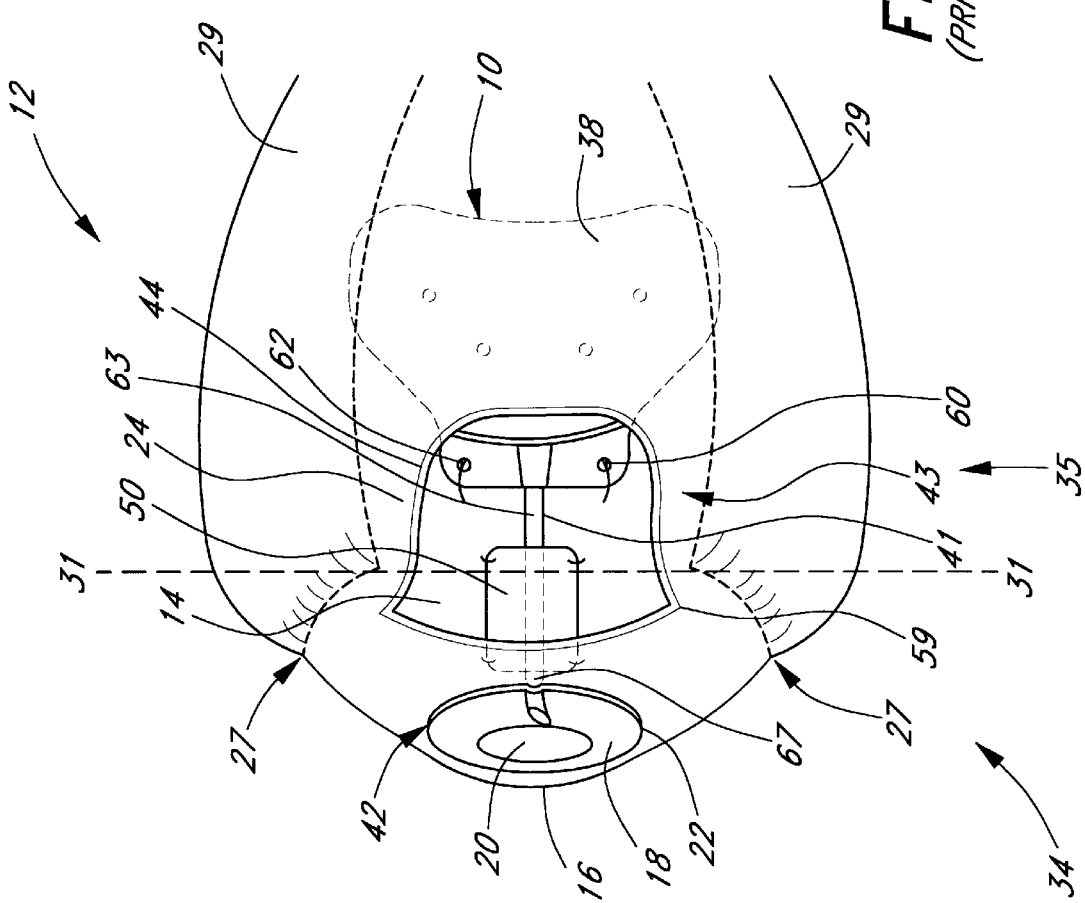
Figure 3A:
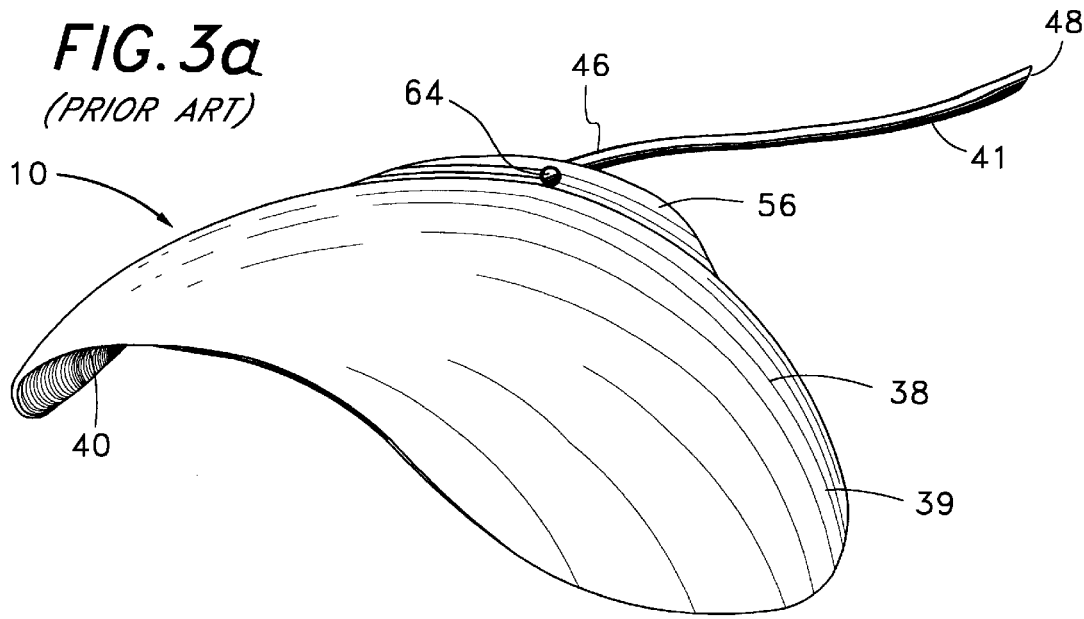
FIGS. 3a–3b are perspective views illustrating one embodiment of the implant of the present invention.
Figure 3B:
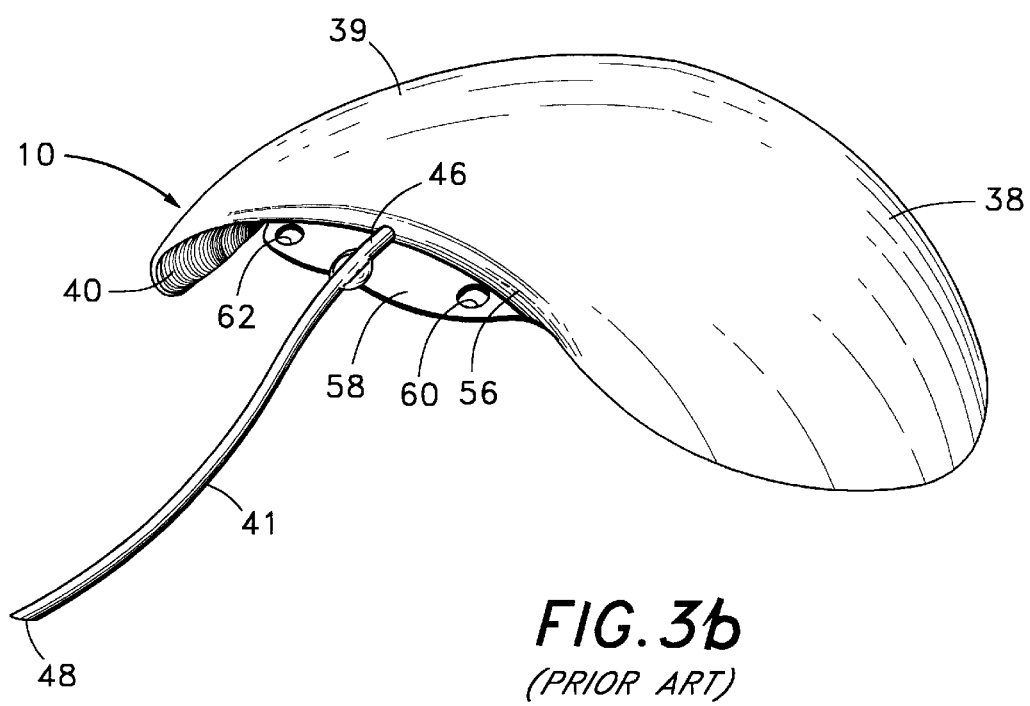

FIG. 1 and FIG. 2 illustrate an implant 10 positioned within the posterior segment 35 of an eye 12, as known in the prior art. The relevant structure of the eye 12 will be described briefly below to provide background for the anatomical terms incorporated herein, however, it should be realized that several anatomical details have been omitted for clarity of understanding. The tough outer membrane known as the sclera 14 covers all of the eye 12 except that portion covered by the cornea 16, the thin, transparent membrane which covers the iris 18 and the pupil 20. The cornea 16 merges into the sclera 14 at a juncture referred to as the sulcus of the sclera or as the limbus 22. A portion of the sclera 14 is covered by a thin tissue called the conjunctiva 24. The ciliary body 26 begins at the limbus 22 and extends along the interior of the sclera 14 and becomes the choroid 28. The choroid 28 is a brown vascular membrane which extends along the retina back toward the optic nerve. The eye includes six extraocular eye muscles which control the movement of the eye in the socket. The eye muscles include the rectus muscles 29 which include lateral, medial, superior, oblique and inferior muscles (the superior and lateral are shown). The muscle insertion 27 is the point at which the rectus muscles 29 attach to the globe of the eye. The dotted-line 31 indicates the boundary between the anterior portion of the globe of the eye, also referred to as the anterior segment 34, and the posterior portion of the globe of the eye, also referred to as the posterior segment 35. The anterior segment 34 is the portion of the globe of the eye which is anterior to the muscle insertions 27. The remainder of the globe which is posterior to the muscle insertions 27 is considered the posterior segment 35.

It is well-known that aqueous is produced by the ciliary body 26 and reaches the anterior chamber 30 formed between the iris 18 and the cornea 16 through the pupil 20. In a normal eye, the aqueous is removed through the trabecular meshwork 32. There the aqueous passes through Schlemm's canal 36 and through veins which merge with blood-carrying veins and into venous circulation. Intraocular pressure is maintained in the eye 12 by the intricate balance of secretion and absorption or outflow of the aqueous in the manner described above. Glaucoma results from excessive buildup of aqueous fluid in the anterior chamber 30 which produces an increase in intraocular pressure.

Implants for treatment of glaucoma facilitate the outflow of the aqueous from the anterior chamber 30 of the eye 12. The implant 10 comprises a pliable plate or spacer 38, also referred to as a pliable seton in the ophthalmic field, having oppositely disposed first 39 and second 40 curved surfaces, connected to a drainage tube 41 which extends into a first region 42 of the eye 12. As illustrated in FIG. 1, the seton 38 is implanted in a second region 43 of the eye 12 beneath a layer of Tenon's capsule 44 and sutured to the sclera 14. More specifically, the implant illustrated in FIGS. 1–2 is implanted in the posterior segment 35 of the eye. The discharge tube 41 comprises a first end 46 and a second end 48 wherein the first end 46 is attached to the plate 38 adjacent the first surface 39 of the plate 38. The second end 48 of the tube 41 extends through the layer of Tenon's capsule 44 and through the cornea 16 into a first region 42 of the eye 12, such as the anterior chamber 30 of the eye 12, to provide fluid communication between the first region 42 and the second region 43 of the eye 12. A scleral reinforcing element 50, such as a connective tissue graft, i.e., a sclera graft, dura mater graft, fascia lata graft, or a graft formed from other biocompatible materials, covers the exposed portion of the tube 41 located between the Tenon's capsule 44 and the cornea 16. A large drainage bleb 52 surrounds the seton 38 and lifts the layer of Tenon's capsule 44 above the sclera 14. The plate 38 acts as a permanent bleb controlling stent to inhibit the tendency of the body to heal itself which would eliminate the bleb. Therefore, the plate 38 is referred to as a bleb formation device or as the bleb formation portion of the implant 10.

One embodiment of the prior art implant 10 is shown in more detail in FIGS. 3a–3c and 4a–4b. The plate 38 is generally spherical in shape and has a perimeter which is elliptical. The surface area of the plate 38 is preferably in the range of approximately 100 to 600 mm² depending on glaucoma conditions and the radius of curvature of the plate 38 is preferably 12 to 14 mm. More preferably, the surface area of the plate 38 is between 250 mm² and 450 mm². When the plate 38 is pressed flat, the plate has a length of between 20–40 mm and a width of 15–20 mm. In the configuration of the plate illustrated in FIG. 3c, the dimensions of the plate 38 when pressed flat are: a length of 32 mm and a width of 14 mm and the resulting surface area of the plate 38 is 343 mm² (+/−7 mm²). Preferably, the length of the plate 38 includes a raised ridge 56 formed adjacent one of the larger-radius perimeter edges of the plate 38, on the first curved spherical surface 39 of the plate 38. The rounded edge of the plate 38 extending on either side of the raised ridge 56, not including that portion of the plate 38 adjacent the ridge 56, is entirely radiused, tapered and blended so as to facilitate insertion as described below. Additionally, the rounded edge of the plate 38 is tapered and blended to discourage the unwanted growth of scar tissue on the plate 38 which may lock the plate 38 into an unwanted position. The rounded edge of the plate 38 provides a smooth surface from which the scar tissue preferably slides off and is therefore unable to completely anchor onto the plate 38. The second surface 40 of the plate 38 is curved to conform to the curvature of the eye 12 and the curvature of the ridge 56 matches the curvature of the sclera 14. An extension 58 of the plate 38 is formed adjacent the ridge 56 in the plate 38 and includes two small suture holes 60, 62. The thickness of the plate 38 is preferably in the range of 0.5 to 2.0 mm. The plate may include fenestrations, or small holes, on the surface of the plate. The fenestrations 61 are shown in the configurations of the implant shown in FIGS. 3c, 4a and 4b.

The drainage tube 41 is coimected to the plate 38 with adhesive, such as Clear Silicone Rubber Adhesive RTV-118 manufactured by General Electric Silicone Products of Waterford, N.Y., via a small hole 64 formed in the ridge 56 and is bonded to the plate 38 using well-known bonding techniques. The first end 46 of the tube 41 thus drains into the recess formed at the junction of the ridge 56 and the smooth first surface 39 of the plate 38. The plate 38 is preferably formed of silicone elastomer, such as SILASTIC™, Medical Grade Q7-4765, 65 Shore A, manufactured by Dow Corning Corporation of Midland, Mich. or Nusil Corp. of Santa Barbara, Calif., although other silicone elastomers in the range of 40–85 Shore A and having good elastic memory are also suitable. The silicone elastomer is filled with a radiopaque material, such as Barium Sulfate, so that the implant is visible in X-ray procedures, thereby allowing patient progress monitoring. The drainage tube 41 is preferably a 1.0 to 3.0 French flow tube, approximately 10 mm to 15 mm in length, formed of SILASTIC™, Medical Grade RX-50, also available from Dow Corning Corporation or Nusil Corp. of Santa Barbara. More preferably, the drainage tube has an inner diameter of 0.30 mm and an outer diameter of 0.60 mm.

Figure 4B:
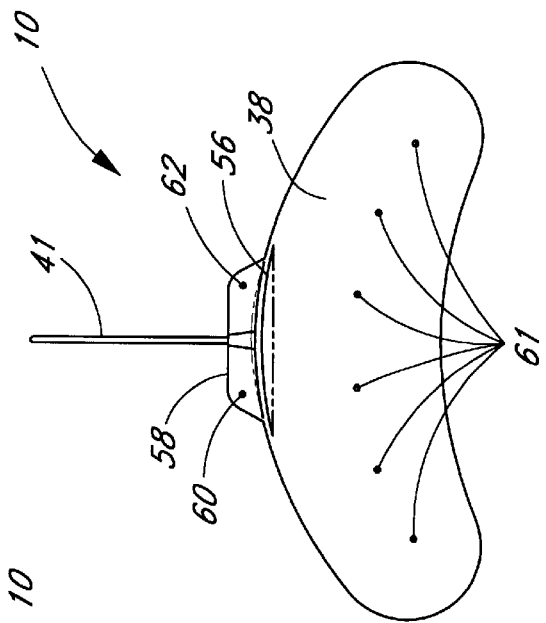
FIG. 4b is a top-plan view of still another configuration of the implant of the present invention.
Figure 4A:
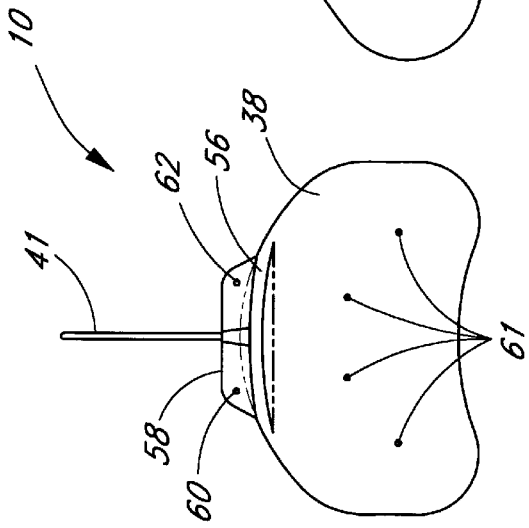
FIG. 4a is a top-plan view of another configuration of the implant of the present invention.
Figure 3C:
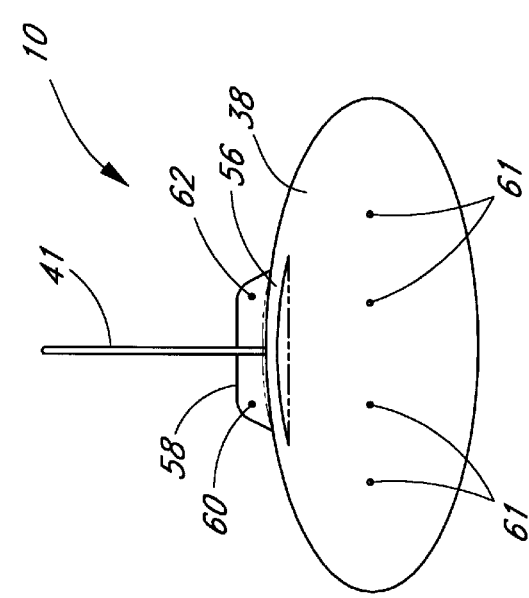
FIG. 3c is a top-plan view of another configuration of the implant of the present invention.

FIGS. 4a–4b illustrate various configurations of the plate 38 of the implant 10 of the present invention. In the configuration of the plate 38 illustrated in FIG. 4a, the dimensions of the plate 38 when pressed flat are: a length of 22 mm and a width of 15 mm and the resulting surface area of the plate 38 is 260 mm$^2$ (+/−5 mm$^2$). In the configuration of the plate illustrated in FIG. 4b, the dimensions of the plate 38 when pressed flat are: a length of 36 mm and a width of 16 mm, and the resulting surface area of the plate 38 is 440 mm$^2$ (+/−9 mm$^2$).

As known in the prior art, the implant 10 can be inserted into the posterior segment 35 of the eye 12 using known ophthalmological surgical techniques and, with reference to FIG. 1 and FIG. 2, the surgical implant procedure will be briefly described. An initial incision 59 is made in the conjunctiva 24 and Tenon's capsule 44 parallel to the limbus 22, the incision is stretched to enable the insertion of the implant 10. The plate 38 is inserted into the second region 43 of the eye 12 through the initial incision 59 and positioned in the posterior segment 35 of the eye beneath the Tenon's capsule 44 and a portion of the superior and lateral rectus muscle 29 or extending totally under one or more of the rectus muscles, thus covering the sclera 14. The plate 38 can be sutured to the sclera 14, or alternatively, to the rectus muscles 29 if the sclera 14 is thinned by disease, with the suture holes 60,62. Preferably, nonabsorbable nylon sutures are used in the suture holes 60, 62 to secure the plate 38, such as a 7-O or 8-O nylon or polypropylene sutures. The drainage tube 41 is tunneled out through the sclera 14 and the cornea 16 beneath Tenon's capsule 44 and in through an incision 65 in the region of the limbus 22 such that the second end 48 of the tube 41 extends into a first region 42, such as the anterior chamber 30, of the eye 12. The exposed portion of the drainage tube 41 is then covered with a scleral reinforcing element 50. In one embodiment, the drainage tube 41 is sutured closed with a temporary suture(s) 63, 67 at a location on either side of the sclera reinforcing element 50 to prevent any drainage of aqueous prior to formation of the bleb tissue 52 over the plate 38. In actual practice, it has been found that initially after surgery aqueous fluid will weep through a space formed between the yet to be healed incision 65 and the drainage tube 41. This weeping of the aqueous fluid through the incision 65 relieves some of the fluid pressure until the bleb 52 has formed and the temporary suture(s) 63, 67 is/are removed or absorbed by the body. In one embodiment, the temporary suture(s) 63 is a dissolvable suture while suture 67 is nonabsorbable. In an alternate, but not preferred, embodiment, the temporary sutures 63, 67 are removed during a secondary procedure, such as a surgical procedure or an ophthalmic laser procedure. Both procedures are known to those of skill in the art.

The formation of the bleb 52 occurs in response to the introduction of the plate 38 into the tissue of the second region 43 of the eye 12. The bleb 52 comprises a thin layer of connective tissue which encapsulates the plate 38, and substantially all of the surfaces of the plate 38 contact the tissues in the second region 43 of the eye 12, thus lifting the Tenon's capsule 44 above the sclera 14 as shown. Typically, bleb 52 formation occurs in the range of 1 to 8 weeks postoperatively. In the above embodiment, an additional surgery can be performed at this time to remove the suture(s) 63, 67 from the drainage tube 41 and allow flow of aqueous from the anterior chamber 30 to the bleb 52 via the drainage tube 41. Alternatively, a dissolving suture can be used to seal the drainage tube 41. After removal or dissolution of the suture(s) 63, 67 blocking the drainage tube 41, the aqueous flow between the tube 41 and bleb 52 is advantageously a patent flow, allowing both flow from the anterior chamber 30 to the bleb 52 and vice versa. This ensures that retrograde non-valved flow from the bleb 52 to the anterior chamber 30, occurring in response to pressure on the eye 12 from the outside, for example, when the lid is forced closed or when the eyeball is pressed on with a finger, does not adversely or harmfully affect intraocular pressure within the eye 12. The fluid contained in the bleb 52 seeps through the bleb into intercellular spaces within the eye 12 and is then removed through surrounding capillaries or lymphatics.

In a preferred embodiment of the present invention illustrated in FIG. 5, the implant 10 of FIG. 4a is implanted in the eye 12 such that a portion of the plate of the implant extends into the anterior segment of the eye. An initial incision 59 is made in the conjunctiva 24 and Tenon's capsule 44 parallel to the limbus 22. The plate 38 is inserted into the second region 43 of the eye 12 through the initial incision 59 and placed between Tenon' Capsule 44 and the sclera 14. The implant 10 is positioned such that at least a portion of the plate 38 extends into the anterior segment 34 of the eye. The remainder of the plate 38, if any, extends into the posterior segment 35 of the eye. Preferably, the surface area of the plate 38 which extends into the anterior segment 34 of the eye 12 is between 10 mm$^2$ and 400 mm$^2$ depending upon the size of the plate 38. More preferably, the surface area of the plate 38 which extends into the anterior segment 34 of the eye 12 is between 28 mm$^2$ and 60 mm$^2$. Anywhere from 5% to 99% of the surface area of the plate 38 can extend into the anterior segment 34 of the eye 12. Preferably, between 5% and 30% of the surface area of the plate 38 can extend into the anterior segment 34 of the eye 12. A portion of the plate 38 is placed below the superior and lateral rectus muscles 29 or extending under one or more of the rectus muscles 29. However, depending upon the surface area of the plate 38, it is possible that no portion of the plate 38 will extend below any of the rectus muscles 29. The plate 38 can be sutured to the sclera 14, or alternatively, to the rectus muscles 29 if the sclera 14 is thinned by disease, with the suture holes 60,62. Preferably, nonabsorbable nylon sutures are used in the suture holes 60, 62 to secure the plate 38, such as a 7-O or 8-O nylon or polypropylene sutures. The drainage tube 41a is tunneled out through the sclera 14 and the cornea 16 beneath Tenon's capsule 44 and in through an incision 65 in the region of the limbus 22 such that the second end 48 of the tube 41a extends into a first region 42, such as the anterior chamber 30, of the eye 12. In one embodiment, the drainage tube 41a is sutured closed with a temporary suture(s) 63, 67 (as shown in FIGS. 1 and 2) to prevent any drainage of aqueous prior to formation of the bleb tissue over the plate 38. In actual practice, it has been found that initially after surgery aqueous fluid will weep through a space formed between the yet to be healed incision 65 and the drainage tube 41a. This weeping of the aqueous fluid through the incision 65 relieves some of the fluid pressure until the bleb has formed and the temporary suture is removed or absorbed by the body. In one embodiment, the temporary suture is a dissolvable suture. In an alternate, but not preferred, embodiment, the temporary suture is removed during a secondary procedure, such as a surgical procedure or an ophthalmic laser procedure. Both procedures are known to those of skill in the art.

Advantageously, the insertion of the implant, such that a portion of the plate 38 extends into the anterior segment, provides for a simpler insertion procedure. First, it is easier to position the plate 38 in the eye 12 when a portion of the plate 38 extends into the anterior segment 34 of the eye, as it is easier for the surgeon to work in the anterior segment 34 of the eye 12. Second, it is easier to suture the plate 38 to the sclera when the suture holes 60, 62 are located in the anterior segment 34 of the eye 12, as the suture holes 60, 62 are easier for the surgeon to access. Finally, by moving a portion of the plate 38 of the implant 10 into the anterior segment 34 of the eye 12, the surface area of the plate 38 can be increased. Thus, a plate 38 can be formed to cover the sclera 14 in the anterior segment 34 and posterior segment 35 of the eye 12. By increasing the surface area of the plate 38, the surface area of the bleb that forms around the plate 38 increases. It has been shown that by increasing the surface are of the bleb that covers the sclera 14, the intraocular pressure can be decreased more significantly. Thus, these implants with an increased surface area will be more effective at treating the most severe cases of glaucoma without requiring additional medications.

The flexible elastomeric material used to form of the present invention, and the size and elliptical shape of the plate 38 allows the implant 10 to be inserted much more easily than previously realized with other glaucoma treatment implants. During the insertion process, the plate 38 can be "folded" in half about the axis of the tube 41 and then inserted through the incision 59. Once placed through the incision 59, the plate 38 will return to its original shape and can be positioned to cover the sclera 14, as described above. Further, the flexible material from which the plate 38 is formed is soft and pliable which results in much less trauma and irritation to the surrounding tissues and vasculature than experienced with a rigid plate device. In addition, since the plate 38 can be folded, a smaller incision can be made in the conjunctive 24 and Tenon's capsule 44. Thus, the pliable plate 38 significantly decreases the surgical procedure length while also minimizing tissue and vasculature damage which can occur in the insertion process.

Figure 6:
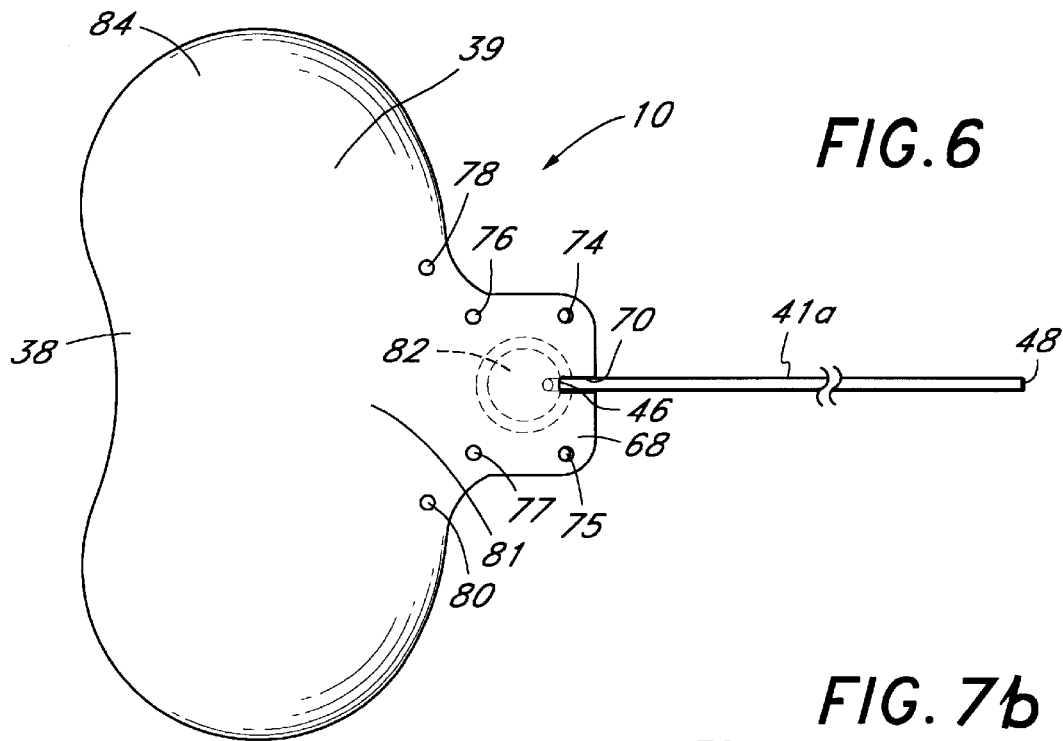
FIG. 6 is a top plan view illustrating the preferred embodiment of the implant.
Figure 7B:
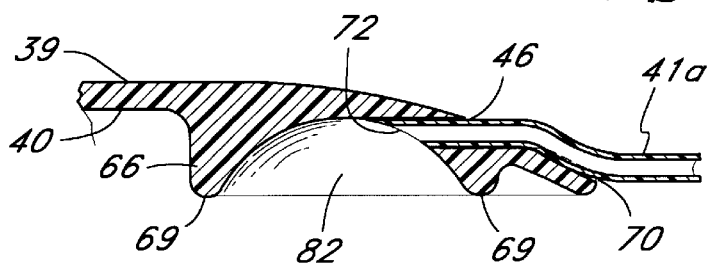
Figure 7A:
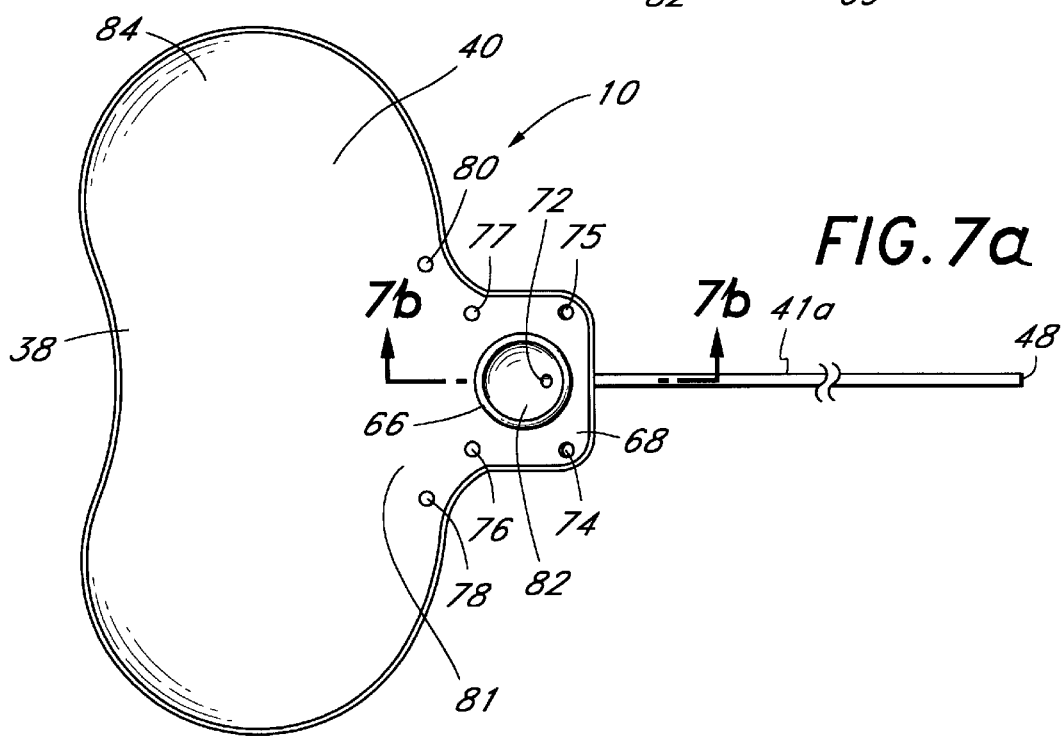
FIG. 7a is a bottom plan view illustrating the preferred embodiment of the implant.

In the preferred embodiment of the implant 10 illustrated in FIG. 6, FIG. 7a and FIG. 7b, the plate 38 has a profile shape that is generally spherical and conforms to the contour of the eye. Preferably, the plate 38 is shaped like the profile of an elongated soybean. The soybean shape is similar to the elliptical shape of FIGS. 3a–3c with a rearward portion of the plate 38 removed. The soybean shape is preferred as the removed rearward portion of the plate 38 prevents the plate 38 from interfering with the optic nerve. As indicated above, the surface area of the plate 38 is preferably in the range of approximately 100 to 600 $mm^2$ depending on glaucoma conditions. A sloped wall 66 extends from the second surface 40 of the plate 38 in a forward portion 68 of the plate 38. The dimensions of the forward portion 68 of the plate 38 in which the sloped wall 66 extends is from 2 to 20 mm in length and from 2 to 20 mm in width. In the preferred embodiment, the dimensions of the forward portion 68 of the plate are 6 mm in length and 4 mm in width. The dimension of the forward portion 68 of the plate 38 could be larger or smaller than those described above to accommodate a cavity 82 of the desired dimensions. Preferably, the sloped wall 66 has a blended and rounded edge to provide a smooth surface from which scar tissue preferably slides off instead of connecting to the wall 66. Desirably, the sloped, blended rounded edge of the wall 66 prevents scar tissue from anchoring onto the implant 10 and permanently tethering the plate 38 to the sclera in an undesired position. The sloped wall 66 is preferably 25 microns to 5 mm thick, i.e., wide and 50 microns to 4 mm in height. The tip of the sloped wall 66 forms a sealing surface 69 which seals against the sclera 14 upon implantation.

The drainage tube 41a is connected to the plate 38 of the preferred embodiment along a first notch 70 formed in the first surface 39 of the plate 38, and then through an opening or small hole 72 formed in the plate 38 which opens into the second surface 40 of the plate 38. The first end 46 of the tube 41a is bonded to the plate 38 along the notch 70 with adhesive, such as Clear Silicone Rubber Adhesive RTV-118 manufactured by General Electric Silicone Products of Waterford, N.Y., and using well-known bonding techniques. The tube 41a is bonded to the hole 72 in the plate 38 such that the first end 46 of the tube 41a is open to the second surface 40 of the plate 38. The drainage tube 41a, as shown in FIGS. 5–10, is preferably a 1.0 to 3.0 French flow tube, approximately 10 mm or less in length, formed of SILASTIC™, Medical Grade RX-50, also available from Dow Corning Corporation or Nusil Corp. of Santa Barbara. More preferably, the drainage tube has an inner diameter of 0.30 mm and an outer diameter of 0.60 mm. The drainage tube 41a of the preferred embodiment is less than 8 mm in length, i.e., shorter than the draining tube 41 illustrated in FIGS. 1–4c which is approximately 10 mm to 15 mm in length. The drainage tube 41 is sized for a plate 38 which is implanted in the posterior segment 35 of the eye 12, while the 41a is sized for implantation such that at least a portion of the plate 38 is positioned in the anterior segment 34 of the eye 12 and therefore does not need to be as long.

The sloped wall 66 completely surrounds the opening 72 in the second surface 40 of the plate 38. Preferably, the sloped wall 66 surrounds an area of approximately 0.08 $mm^2$–75 $mm^2$ around the opening 72 in the second surface 40 of the plate 38. More preferably, the sloped wall 66 surrounds an area of approximately 2 mm$^2$–14 mm$^2$ around the opening 72 in the second surface 40 of the plate 38. In the preferred embodiment, the sloped wall 66 is annular in shape to evenly surround the opening 72 and the diameter of the annular shape covered by the wall is preferably between approximately 1 mm to 4 mm, but could be as large as 15 mm. In the preferred embodiment, the annular sloped wall forms a concave cupped cavity 82 as defined by the sloped wall 66 and the second surface 40 of the plate 38. As will be recognized by one of skill in the art, the sloped wall 66 may take on a variety of shapes, such as oval, heart shaped, square, rectangular, triangular, etc., in most cases the shape surrounds the opening 72 in the second surface 40 of the plate 38. A first plurality of suture holes 74–77 are provided around the sloped wall 66. In the preferred embodiment, the first plurality of sutures holes 74–77 are evenly spaced around the perimeter of the forward portion 68 of the plate 38. A second plurality of suture holes 78, 80 are provided in an intermediate portion 81, proximal to the forward portion 68, of the plate 38 to enable a surgeon to further secure the plate 38 to the sclera 14 (FIG. 8).

Figure 8:
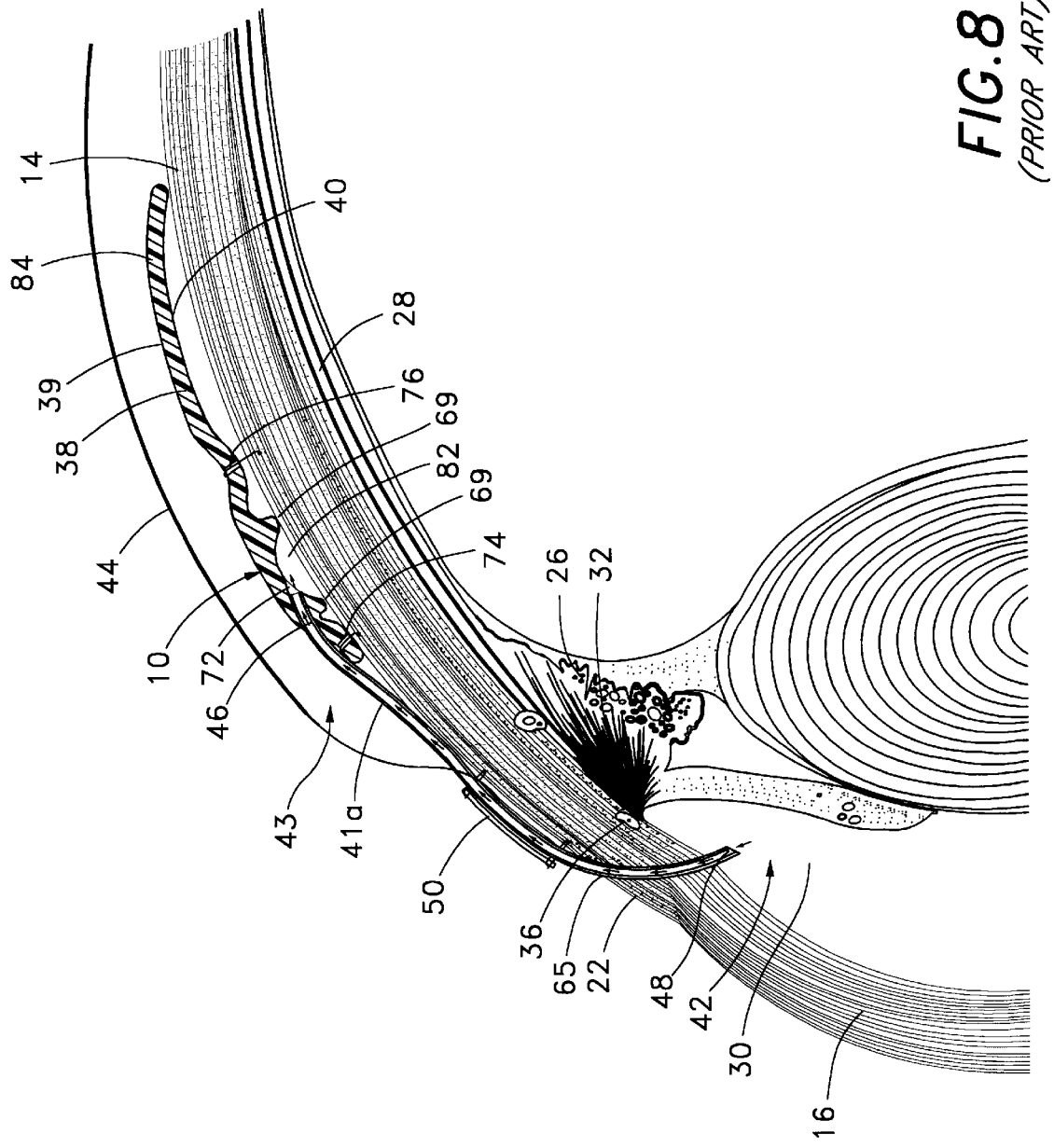
FIG. 8 is a cross-sectional view of the implant of FIG. 6 and FIGS. 7a–7b implanted in the posterior segment of the eye immediately after surgery where both the implant and its placement are prior art.

Referring also to FIG. 8, when an implant 10 is inserted into the posterior segment 35 of the eye 12, utilizing the procedure described above, the plate 38 is inserted into the second region 43 of the eye and positioned beneath the Tenon's capsule 44 and a portion of the lateral and superior rectus muscles (FIG. 2), thus covering the sclera 14. The tip of the sloped wall 66 creates a sealing surface 69 against the sclera 14. Preferably, the seal is similar to an o-ring seal. By positioning the implant 10 such that the lateral and superior rectus muscles 29 are covering a portion of the implant 10, the rectus muscles 29 helps hold the implant 10 against the sclera 14 but does not create any portion of the desired seal. Depending upon the size of the plate 38, it is possible that the plate 38 may not extend under any of the rectus muscles or it may extend under one or more of the rectus muscles (FIG. 2). The implant 10 lies between the sclera 14 and Tenon's capsule 44. Tenon's Capsule 44 lies on the upper surface 39 of the plate 38, but Tenon's Capsule 44 does not create a portion of the desired seal. During implantation, the plate 38 is sutured to the sclera 14 utilizing both absorbable and nonabsorbable sutures in a first plurality of suture holes 74–77 and absorbable or nonabsorbable sutures in a second plurality of suture holes 78, 80. The first plurality of suture holes 74–77 are spaced around the sloped wall 66 to provide an enhanced seal of the wall 66 against the sclera 14. The second plurality of sutures 78,80 on the immediate portion 81 of the plate 38 assist in tethering the plate 38 to the sclera 14. After implantation, the aqueous fluid from the first region 42 of the eye 12 drains through the drainage tube 41a into the concave cupped cavity 82 which is sealed against the sclera 14. The sutures 74–77 assist in sealing the cupped cavity 82 against the sclera 14 at the sealing surface 69; therefore, the aqueous fluid is unable to escape from the cavity 82. Once the cavity 82 is filled with fluid, the fluid pressure within the scaled cavity 82 prevents additional fluid from draining from the first region 42 of the eye 12 into the cavity 82, thereby preventing low pressure from occurring in the second region 42 of the eye 12. As will be recognized by those of skill in the art, the dimensions of the cavity 82 are selected to define the flow of fluid that can exit the first region 42 of the eye 12, before the flow is restricted, without creating a pressure drop in the eye 12. Therefore, the sealing of the wall 66 of the plate 38 against the sclera 14 creates a sealed cavity 82 which temporarily occludes the drainage of aqueous fluid from the first region 42 of the eye 12.

The o-ring seal effect is achieved both by the design of the implant 10 and the tension produced by the absorbable and nonabsorbable sutures placed by the surgeon in the first plurality of suture holes 74–77 and/or the second plurality of suture holes 78, 80. The sutures hold the implant 10 against the sclera 14 with the necessary tension desired by the surgeon. In a preferred embodiment, the tension level of the sutures is set to withstand pressures of up to 10–20 mm mercury. Preferably, the fluid pressure in the first region 42 of the eye 12 reaches an equilibrium pressure with the pressure in the cavity 82 while scar tissue in the eye forms a bleb 52. This equilibrium pressure is less than the pressure applied by the sutures. Further, some fluid in the cavity 82 may be absorbed by the sclera tissue below the cavity 82. This absorption of fluid will help maintain the desired equilibrium pressure. When the pressure in the cavity 82 and the first region 42 of the eye 12 exceed the tension of the sutures as applied by the surgeon, fluid will leak around the o-ring seal and maintain the eye pressure determined by the surgeon. This prevents the eye pressure from exceeding a specific value, as determined by the tension of the sutures as applied by the surgeon, which could cause damage to the eye. If the fluid pressure does not exceed the tension of the sutures, the o-ring type seal will maintain the fluid pressure within the cavity 82.

Figure 9:
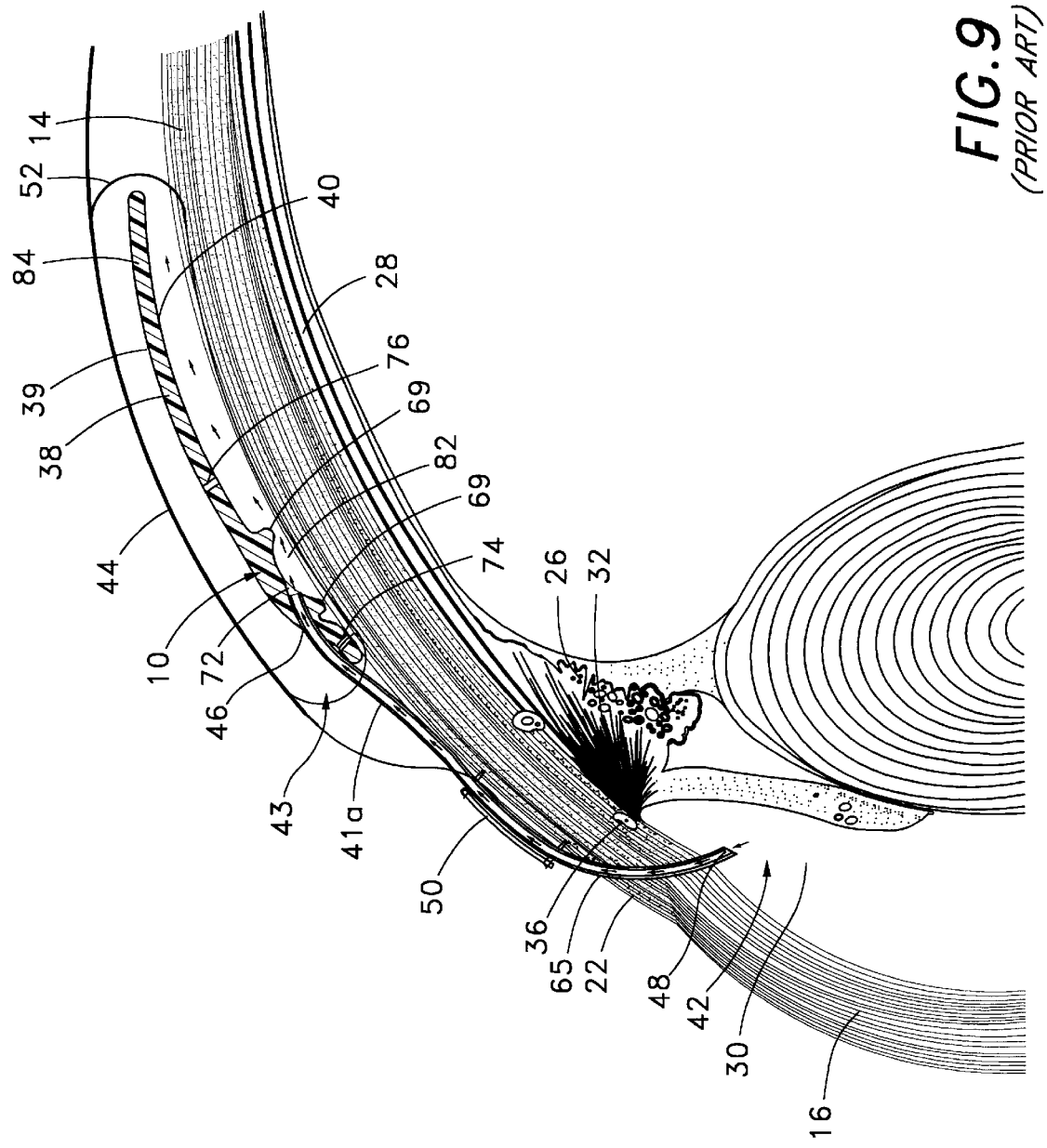
FIG. 9 is a cross-sectional view of the implant of FIG. 6 and FIGS. 7a–7b implanted as in the prior art in the posterior segment of the eye after bleb formation occurs.

Preferably, the temporary sutures are dissolvable sutures. Alternatively, the temporary sutures are removed during a secondary procedure, such as a surgical procedure or a laser procedure, after scar tissue formation. Preferably, the temporary sutures are selected such that the sutures dissolve after the formation of the scar tissue bleb. The sutures can be absorbed at any time postoperatively from 1 day up to 8 weeks. Preferably, the sutures are dissolved in 1 to 6 weeks postoperatively. In the preferred embodiment, the dissolving sutures are 7-O or 8-O Vicryl. As illustrated in FIG. 9, after the bleb 52 forms, the temporary sutures are removed or absorbed by the body, the fluid pressure in the cupped cavity 82 pushes the plate 38 off the surface of the sclera 14 and the seal formed by the sealing surface 69 of the sloped wall 66 against the sclera 14 is broken. The bleb 52 eventually fills with fluid and the seton 38 floats within the fluid in the bleb 52 and maintains the bleb shape. In a preferred embodiment, permanent sutures are utilized in the suture holes 78, 80 on the plate 38 to keep the intermediate end 81 of the seton 38 tethered to the sclera 14 thus preventing the plate 14 from impinging on the eye socket and other tissues in the eye 12 or from extruding. Preferably, with the intermediate end 81 of the plate 38 permanently sutured to the sclera 14, a rearward end 84 of the plate 38 pivots off of the sclera 14. In one embodiment, the tethered plate 38 acts like a leaflet valve. Once the o-ring type seal of the wall 66 is broken, patent flow between the second region 43 of the eye 12, such as the bleb 52, and the first region 42 of the eye 12, such as the anterior chamber 30, is maintained.

Figure 10A:
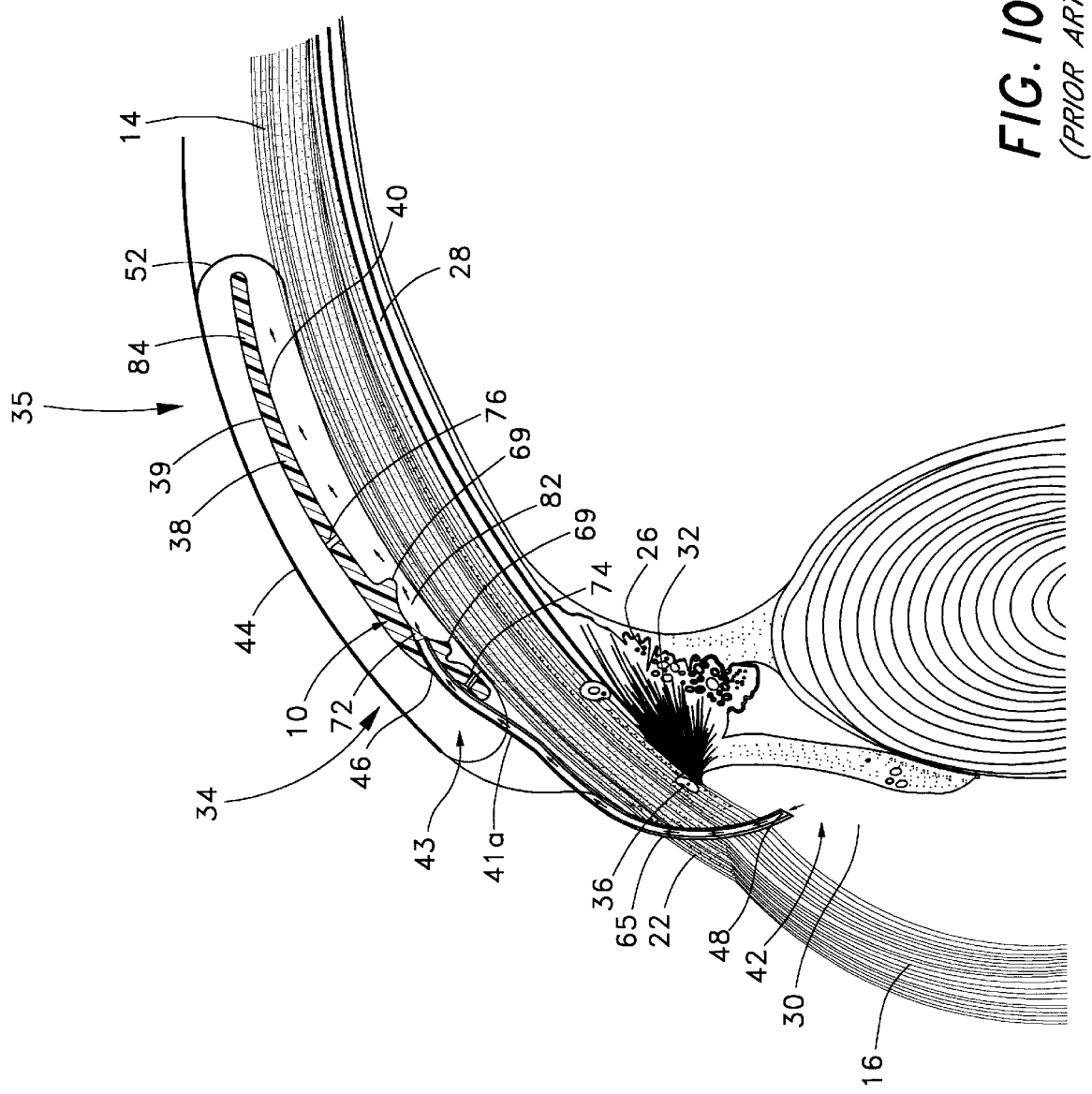
FIG. 10a is a cross-sectional view of the implant of FIG. 6 and FIGS. 7a–7b implanted in accordance with the present invention in a human eye, such that a portion of the plate of the implant extends into the anterior segment of the eye after bleb formation occurs.

Referring to FIGS. 10 and 10a, a preferred insertion technique of the implant 10 of the preferred embodiment is used together with known ophthalmological surgical techniques and is briefly described. An initial incision 59 is made in the conjunctiva 24 and Tenon's capsule 44 parallel to the limbus 22, the incision is stretched slightly to enable the insertion of the implant 10. The plate 38 is inserted into the second region 43 of the eye and positioned between Tenon's capsule 44 and the sclera 14. The implant 10 is positioned such that at least a portion of the plate 38 extends into the anterior segment 34 of the eye. The remainder of the plate 38, if any, extends into the posterior segment 35 of the eye. Preferably, the surface area of the plate 38 which extends into the anterior segment 34 of the eye 12 is between 10 mm² and 400 mm² depending upon the size of the plate 38. More preferably, the surface area of the plate 38 which extends into the anterior segment 34 of the eye 12 is between 28 mm² and 60 mm². Anywhere from 5% to 99% of the surface area of the plate 38 can extend into the anterior segment 34 of the eye 12. Preferably, between 5% and 30% of the surface area of the plate 38 can extend into the anterior segment 34 of the eye 12. A portion of the plate 38 may be placed below the superior and lateral rectus muscles 29 or extending under one or more of the rectus muscles 29. However, depending upon the surface area of the plate 38, it is possible that no portion of the plate 38 will extend below any of the rectus muscles 29.

The drainage tube 41a is tunneled out through the sclera 14 and the cornea 16 beneath Tenon's capsule 44 and in through an incision 65 in the region of the limbus 22 such that the second end 48 of the tube 41a extends into a first region 42, such as the anterior chamber 30, of the eye 12. In one embodiment, the drainage tube 41 is sutured closed with a temporary suture(s) to prevent any drainage of aqueous prior to formation of the bleb tissue 52 over the plate 38. In actual practice, it has been found that initially after surgery aqueous fluid will weep through a space formed between the yet to be healed incision 65 and the drainage tube 41a. This weeping of the aqueous fluid through the incision 65 relieves some of the fluid pressure until the bleb 52 has formed and the temporary suture(s) is/are removed or absorbed by the body. In one embodiment, the temporary suture(s) is/are a dissolvable suture. In an alternate, but not preferred, embodiment, the temporary sutures are removed during a secondary procedure, such as a surgical procedure or an ophthalmic laser procedure. Both procedures are known to those of skill in the art.

In an alternate embodiment, the drainage tube 41a is tunneled through the pars plana which is located 1–3.5 mm behind the limbus into the vitreous cavity (the area behind the lens of the eye).

The tip of the sloped wall 66 creates a sealing surface 69 against the sclera 14. The implant 10 lies between the sclera 14 and Tenon's capsule 44. Tenon's Capsule 44 lies on the upper surface 39 of the plate 38, but Tenon's Capsule 44 does not create a portion of the desired seal. During implantation, the plate 38 is sutured to the sclera 14 utilizing both absorbable and nonabsorbable sutures in a first plurality of suture holes 74–77 and absorbable or nonabsorbable sutures in a second plurality of suture holes 78, 80. The first plurality of suture holes 74–77 are spaced around the sloped wall 66 to provide an enhanced seal of the wall 66 against the sclera 14. The second plurality of sutures 78,80 on the immediate portion 81 of the plate 38 assist in tethering the plate 38 to the sclera 14.

After implantation, the aqueous fluid from the first region 42 of the eye 12 drains through the drainage tube 41a into the concave cupped cavity 82 which is sealed against the sclera 14. The sutures 74–77 assist in sealing the cupped cavity 82 against the sclera 14 at the sealing surface 69; therefore, the aqueous fluid is unable to escape from the cavity 82. Once the cavity 82 is filled with fluid, the fluid pressure within the sealed cavity 82 prevents additional fluid from draining from the first region 42 of the eye 12 into the cavity 82, thereby preventing low pressure from occurring in the second region 42 of the eye 12. As will be recognized by those of skill in the art, the dimensions of the cavity 82 are selected to define the flow of fluid that can exit the first region 42 of the eye 12, before the flow is restricted, without creating a pressure drop in the eye 12. Therefore, the sealing of the wall 66 of the plate 38 against the sclera 14 creates a sealed cavity 82 which temporarily occludes the drainage of aqueous fluid from the first region 42 of the eye 12.

As indicated above, the o-ring seal effect is achieved both by the design of the implant 10 and the tension produced by the absorbable and nonabsorbable sutures placed by the surgeon in the first plurality of suture holes 74–77 and/or the second plurality of suture holes 78, 80. The sutures hold the implant 10 against the sclera 14 with the necessary tension desired by the surgeon. In a preferred embodiment, the tension level of the sutures is set to withstand pressures of up to 10–20 mm mercury. Preferably, the fluid pressure in the first region 42 of the eye 12 reaches an equilibrium pressure with the pressure in the cavity 82 while scar tissue in the eye forms a bleb 52. This equilibrium pressure is less than the pressure applied by the sutures. Further, some fluid in the cavity 82 may be absorbed by the sclera tissue below the cavity 82. This absorption of fluid will help maintain the desired equilibrium pressure. When the pressure in the cavity 82 and the first region 42 of the eye 12 exceed the tension of the sutures as applied by the surgeon, fluid will leak around the o-ring seal and maintain the eye pressure determined by the surgeon. This prevents the eye pressure from exceeding a specific value as determined by the tension of the sutures as applied by the surgeon, which could cause damage to the eye. If the fluid pressure does not exceed the tension of the sutures, the o-ring type seal will maintain the fluid pressure within the cavity 82.

As indicated above, the temporary sutures of the preferred embodiment are dissolvable sutures. In an alternate, but not preferred embodiment, the temporary sutures are removed during a secondary procedure, such as a surgical procedure or a laser procedure, after scar tissue formation. In the preferred embodiment, the temporary sutures are selected such that the sutures dissolve after the formation of the scar tissue bleb. The sutures can be absorbed at any time postoperatively from 1 day up to 8 weeks. Preferably, the sutures are dissolved in 1 to 6 weeks postoperatively. In the preferred embodiment, the dissolving sutures are 7-O or 8-O Vicryl.

After the bleb 52 forms, the temporary sutures are removed or absorbed by the body, the fluid pressure in the cupped cavity 82 pushes the plate 38 off the surface of the sclera 14 and the seal formed by the sealing surface 69 of the sloped wall 66 against the sclera 14 is broken. The bleb 52 eventually fills with fluid and the seton 38 floats within the fluid in the bleb 52 and maintains the bleb shape. In a preferred embodiment, permanent sutures are utilized in the suture holes 78, 80 on the plate 38 to keep the intermediate end 81 of the seton 38 tethered to the sclera 14 thus preventing the plate 14 from impinging on the eye socket and other tissues in the eye 12 or from extruding. Preferably, with the intermediate end 81 of the plate 38 permanently sutured to the sclera 14, a rearward end 84 of the plate 38 pivots off of the sclera 14. In one embodiment, the tethered plate 38 acts like a leaflet valve. Once the o-ring type seal of the wall 66 is broken, patent flow between the second region 43 of the eye 12, such as the bleb 52, and the first region 42 of the eye 12, such as the anterior chamber 30, is maintained. Preferably, at least a portion of the bleb 52 is formed in the anterior segment 34 of the eye 12. The remainder of the bleb, if any, is formed in the posterior segment 35 of the eye.

As indicated above, the insertion of the implant 10 such that a portion of the plate 38 extends into the anterior segment 34 of the eye provides for a simpler insertion procedure. First, it is easier to position the plate 38 in the eye 12 when a position of the plate 38 extends into the anterior segment 34 of the eye, as it is easier for the surgeon to work in the anterior segment 34 of the eye 12. Second, it is easier to suture the plate 38 to the sclera when the suture holes 74–80 are located in the anterior segment 34 of the eye 12, as the suture holes 74–80 are easier for the surgeon to access. Finally, by moving a portion of the plate 38 of the implant 10 into the anterior segment 34 of the eye 12, the surface area of the plate 38 can be increased. Thus, a plate 38 can be formed to cover a portion of the sclera 14 in the anterior segment 34 and posterior segment 35 of the eye 12. By increasing the surface area of the plate 38, the surface area of the bleb that forms around the plate 38 increases. It has been shown that by increasing the surface are of the bleb that covers the sclera 14, the intraocular pressure can be decreased more significantly. Thus, these implants with an increased surface area will be more effective at treating the most severe cases of glaucoma without requiring additional medications.

Figure 13:
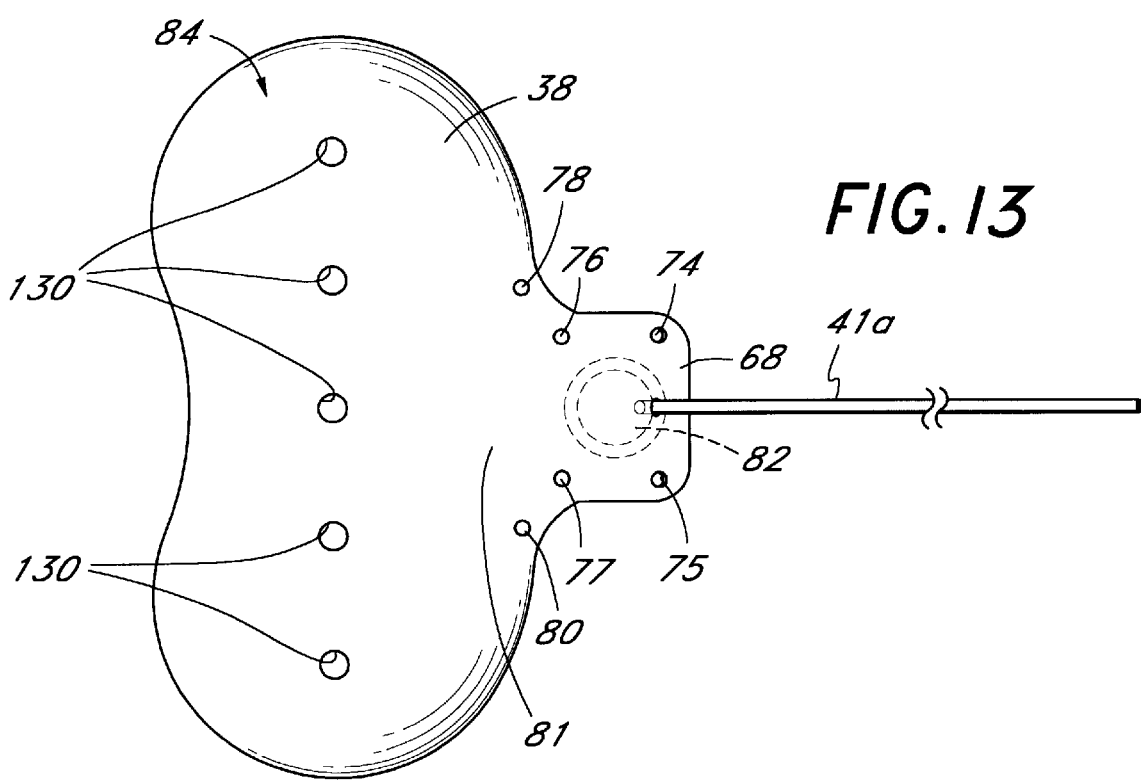
FIG. 13 is a perspective view of an additional alternative embodiment of the implant of the present invention.

FIG. 11 is a cut-away view which illustrates an implant similar to the implant of FIGS. 6 and 13, but having a plate 38 with a larger surface area implanted in a human eye. Preferably, the plate 38 illustrated in FIG. 11 has a surface area of 425 mm². The implant 10 is positioned in the eye, such that a portion of the plate 38 of the implant 10 extends into the anterior segment 34 of the eye 12. In comparison to the implant shown in FIG. 10, a larger surface are of the plate 38 extends into the anterior segment 34 of the eye. Further, a larger surface are of the plate 38 extends below the lateral and superior rectus muscles 29. Preferably, at least 80 mm² of the surface area of the plate 38 extends into the anterior segment 35 of the eye.

Figure 12A:
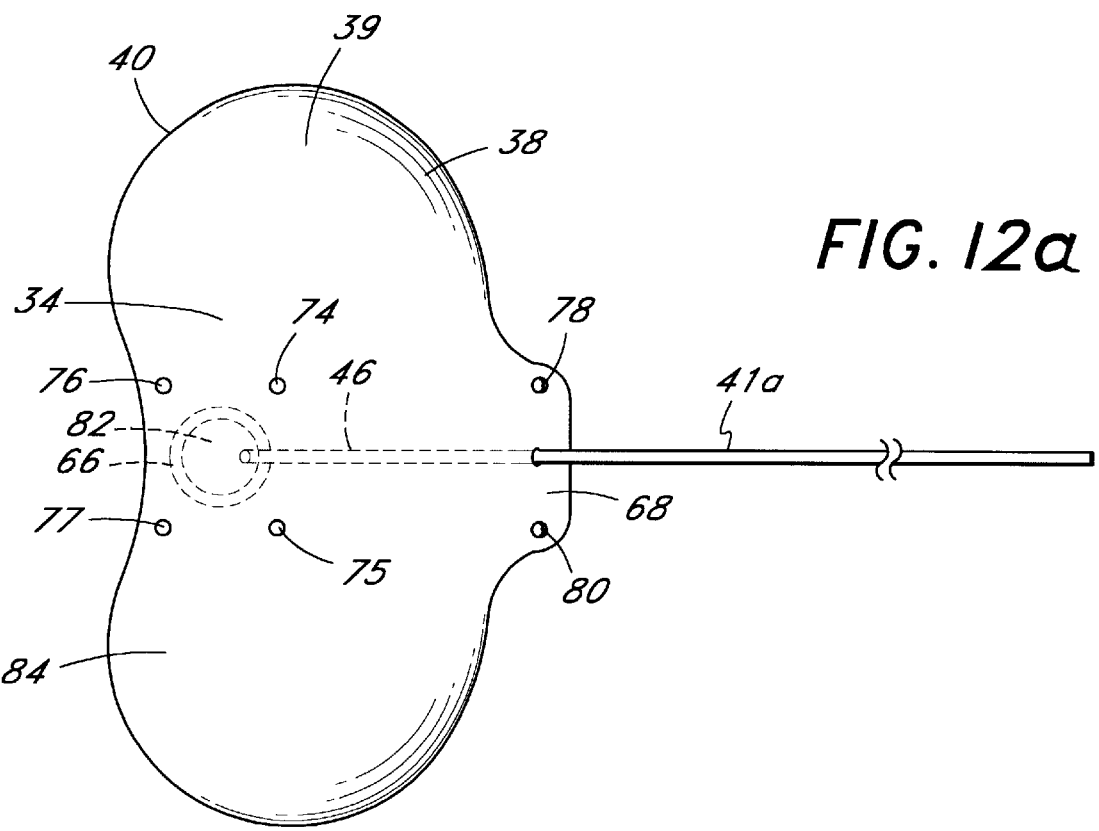
FIGS. 12a through 12c are perspective views illustrating various configurations of the implant of FIG. 6.
Figure 12B:
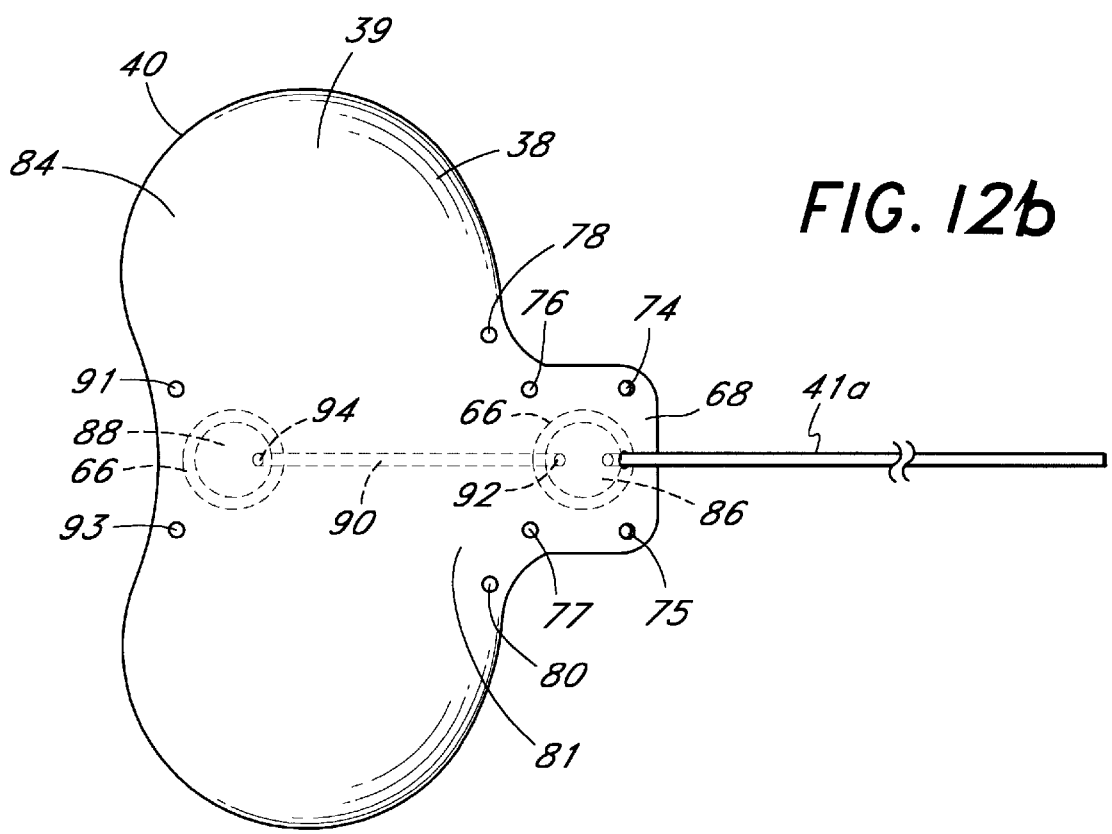
Figure 12C:
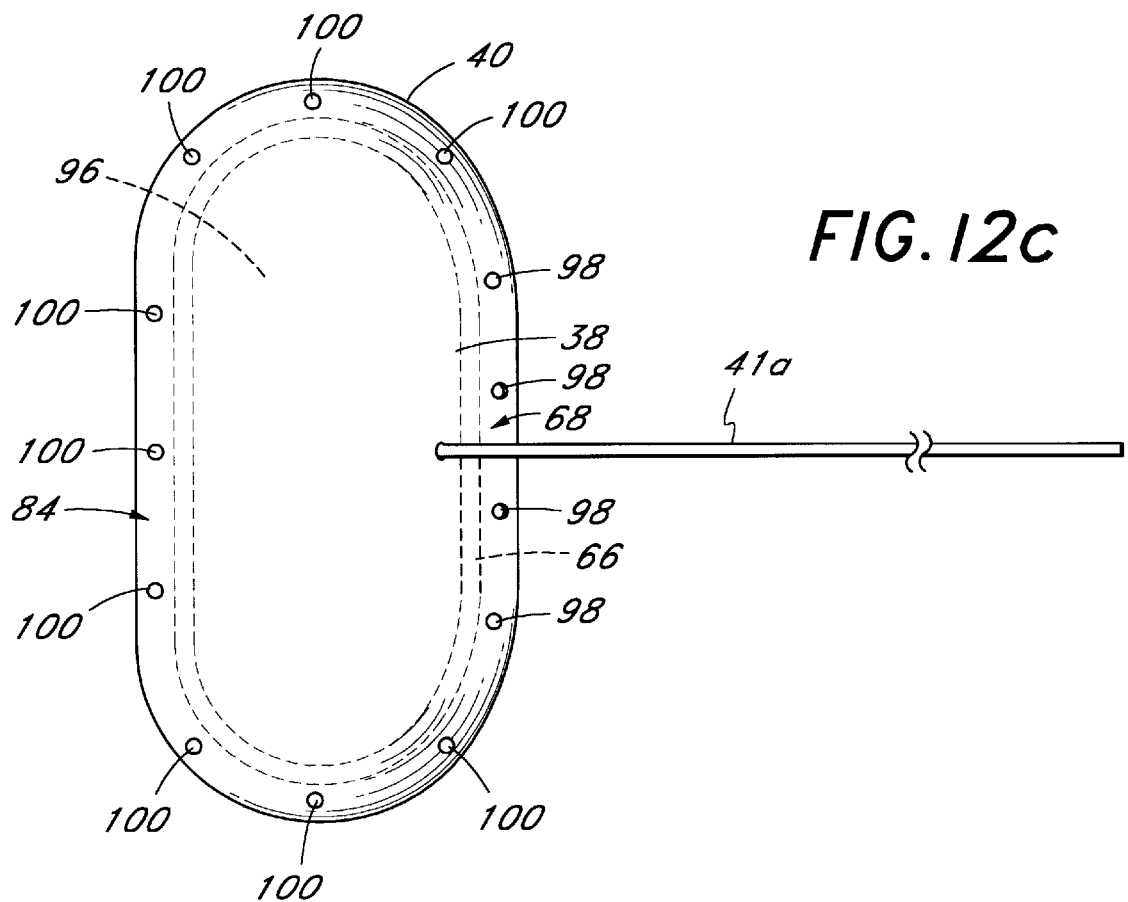

As shown in FIGS. 12a through 12c, a variety of configurations of the sloped wall 66 are possible. Although four configurations are illustrated, one skilled in the art will recognize that various other embodiments could be constructed. The various configurations of the implant 10 illustrated in FIGS. 12a through 12c can be implanted in the anterior segment 34 of the eye 12 as described in association with FIGS. 10 and 11 above or in the posterior segment 35 of the eye 12 as described in association with FIGS. 8 and 9 above. In the embodiment illustrated in FIG. 12a, the concave cavity 82 formed by the sloped wall 66 and the second surface 40 of the plate 38 is located in the rearward end 84 of the plate 38. In this embodiment, the tube 41a is attached along the second surface 40 of the plate 38. The tube 41a preferably enters the cavity 82 through a hole (not shown) in the sloped wall 66. The first end 46 of the tube 41a is open to the cupped cavity 82 formed by the sloped wall 66 and the second surface 40 of the plate 38. In this embodiment, the second plurality of suture holes 78–80 are located on the perimeter of the forward portion 68 of the plate 38, while the first plurality of suture holes 74–77 are located on a rearward portion 84 of the plate 38 surrounding the sloped wall 66. Preferably, the plate 38 is attached to the sclera by temporary sutures in suture holes 74–77 and nonabsorbable sutures in the suture holes 78, 80. Preferably, after bleb formation, the temporary sutures in the rearward portion 84 of the plate 38 dissolve and the rearward portion 68 of the plate 38 floats in the bleb while the forward portion of the plate 38 remains attached to the sclera.

In the embodiment of FIG. 12b, a plurality of cavities defined by the sloped walls 66 are formed on the second surface 40 of the plate 38. First 86 and second 88 cavities are connected by a second flexible elastomeric connection tube 90. Preferably, the first end 46 of the drainage tube 41a is open to the first cavity 86. A first end 92 of the connection tube 90 is open to a hole in the first cavity 86. A second end 94 of the connection tube 90 is open to a hole in the second cavity 88. Once both the first 86 and second 88 cavities are filled with aqueous fluid, the fluid pressure in the cavities 86, 88 prevents additional fluid from draining from the anterior chamber 30 of the eye 12. In this embodiment, a third plurality of suture holes 91, 93 are located on the perimeter of the rearward portion 84 of the plate 38. The plate 38 is attached to the sclera by temporary sutures in the first and third plurality of suture holes 74–77 and 91, 93 and nonabsorbable sutures in the second plurality of suture holes 78, 80. Preferably, after bleb formation, the temporary sutures are absorbed by the body, or alternatively removed, and the rearward portion 84 and a portion of the forward portion 68 of the plate 38 float while the intermediate portion 81 of the plate 38 remains attached to the sclera.

In the embodiment of FIG. 12c, one large cavity 96 is formed below substantially the entire second surface 40 of the plate 38 by the addition of the sloped wall 66 around the entire perimeter of the second surface 40 of the plate 38. Permanent sutures are utilized in the suture holes 98 to affix the forward end 68 of the plate 38 to the sclera. A plurality of suture holes 100 are evenly dispersed around the remaining perimeter of the plate 38. Temporary sutures are used in suture holes 100 to temporarily seal the majority of the perimeter of the plate 33. When the temporary sutures 100 dissolve or alternatively are removed, the rearward portion 84 of the plate 38 lifts off of the sclera 14 to enable patent flow of the aqueous humor from the first region 42 of the eye 12 into the bleb 52.

Figure 12D:
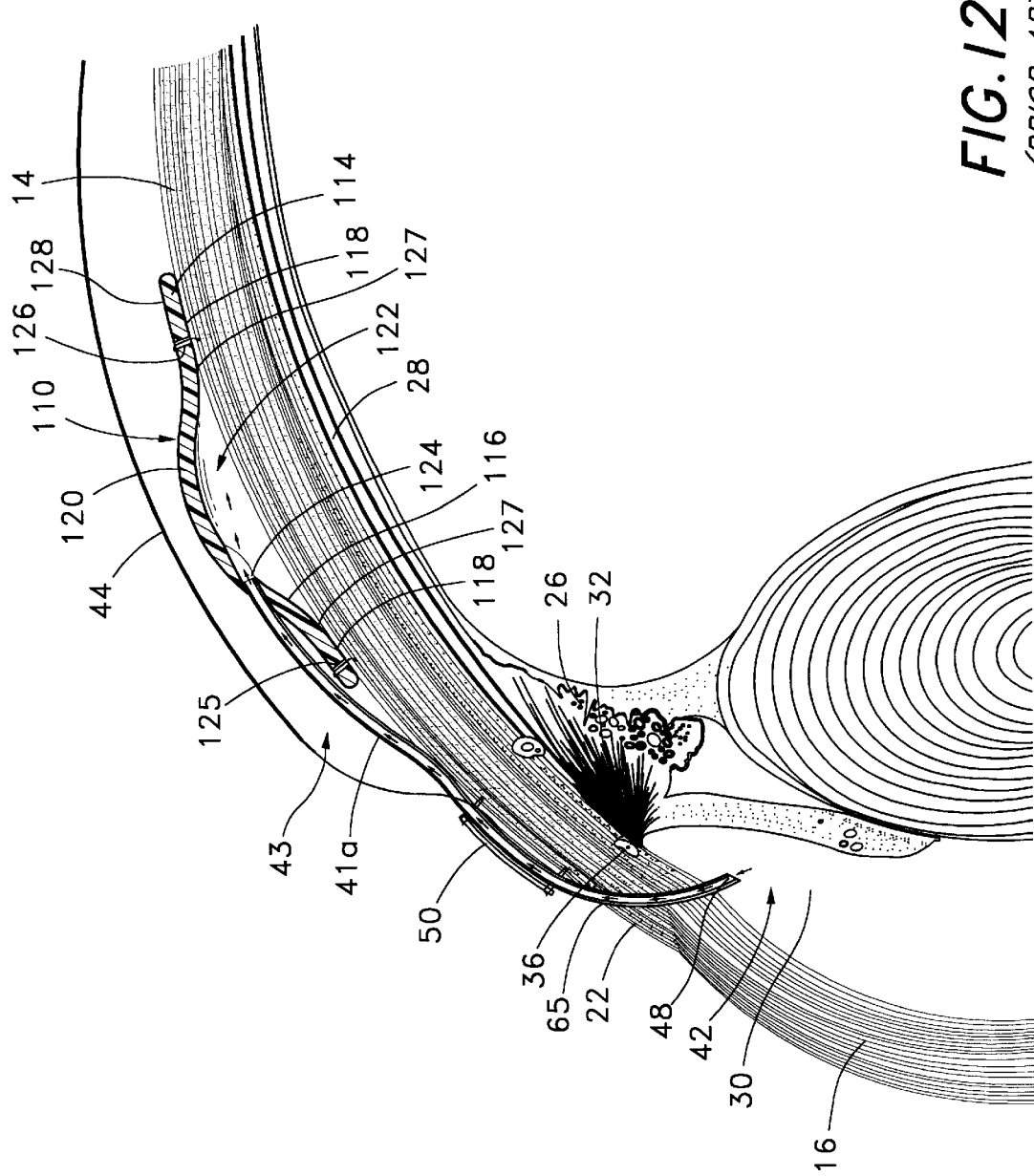
FIG. 12d is a cross-sectional view illustrating another configuration of the implant of FIG. 6 implanted in the posterior segment of the eye immediately after surgery.
Figure 12E:
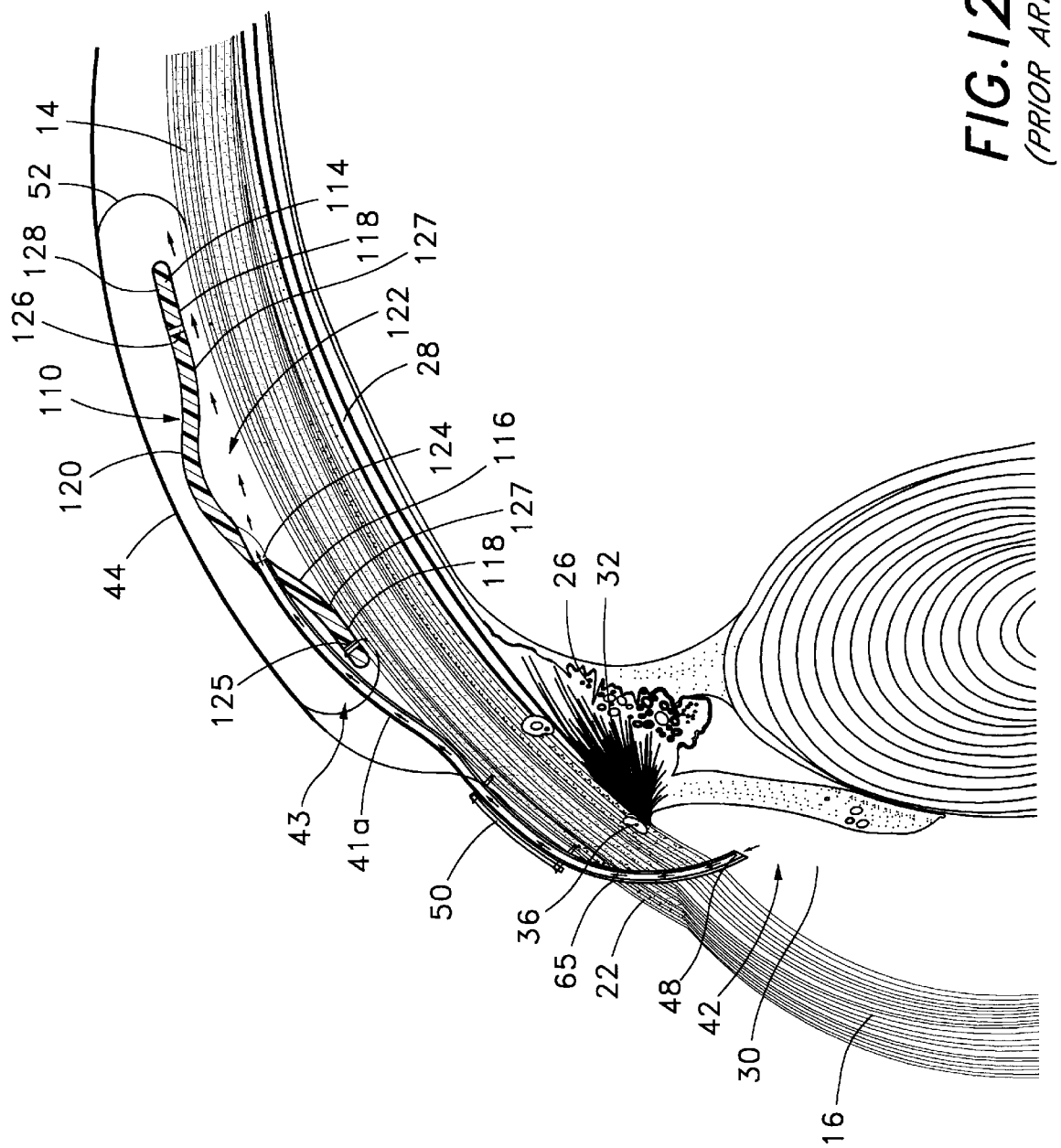
FIG. 12e is a cross-sectional view of the implant of FIG. 12d implanted in the posterior segment of the eye after bleb formation occurs.

In the embodiment of FIGS. 12d–12e, the shape of the implant 110 is modified to form a cavity 122 within the plate, or seton, 114, rather than including a sloped wall extending from a second surface 116 of the plate 114. The plate 114 is shown implanted in the posterior 35 segment of the eye 12, but can be implanted in the anterior segment 34 of the eye 12 as described in association with FIGS. 10 and 11 above. The plate 114 preferably is spherically shaped to match the convex anatomy of the eye and has a matching surface 118 around the perimeter of the concave second surface 116 of the plate 114. In a center portion 120 of the plate 114, the plate 114 is shaped such that a hemispherical cupped concave cavity 122 is formed around an opening 124 of the tube 41a in the second surface 116 of the plate 114. In an alternate embodiment (not shown), the plate 114 does not have to include a hemispherical concave cavity 122 formed in the plate 114. Rather, since the plate 114 is pliable, the plate 114 bends to accommodate the physical anatomical convex shape of the patient's eye 12 such that the matching surface 118 around the perimeter of plate is flush with the surface of the sclera 14. A permanent suture is used in suture hole 125 and a temporary suture is used in suture hole 126 to hold the sealing surface 127 of the seton 114 against the surface of the sclera 14. A sealing surface 127 on the matching surface 118 of the plate is formed against the surface of the sclera 14 which temporarily occludes the flow of the aqueous out of the cavity 122. In the embodiment of the plate 114 where a physical cavity 122 is not formed in the plate, the pliable nature of the sutured plate 114 will naturally form a cavity 122 of sufficient size to hold the desired amount of fluid. As illustrated in FIG. 12e, when the temporary suture in suture hole 126 is removed or absorbed by the body, a rearward portion 128 of the seton 114 moves away from the sclera 14 breaking the seal of the sealing surface 127 against the sclera 14, so that non-valved patent flow of the aqueous can occur.

Another alternative embodiment of the present invention is illustrated in FIG. 13 which incorporates a plurality of holes, sometimes referred to as fenestrations, 130 in the rearward portion 84 of the plate 38 which does not contain the cavity 82. As illustrated in FIG. 13, the plate 38 has essentially the same shape as the embodiments illustrated in FIGS. 6, 7a and 7b, with the addition of a plurality of aligned holes 130 in the rearward portion 84 of the plate 38. The holes 130 do not interfere with the sealed cavity 82 in the forward portion 68 of the plate 38. However, in the preferred embodiment, once the sutures in the first plurality of suture holes 74–77 around the sealed cavity 82 or the second plurality of suture holes 78, 80 dissolve or are removed and the rearward end 84 of the plate 38 is able to float within the bleb, each of the holes 130 will form a dimple in the bleb by permitting scar tissue growth through each of the holes 130. The overall height of the bleb will be significantly decreased in both the upper and lower directions as the bleb is pulled towards the plate 38 by the growth of scar tissue through each of the holes 130. Preferably, the holes 130 are between 50 microns and 10 mm in diameter. As the number of holes 130 in the plate 38 increases, preferably the diameter of the holes 130 decreases proportionally, but will remain within the above range of preferable diameters. As the number of holes 130 increase in the seton 38, the number of dimples in the resulting drainage bleb will increase proportionately until the horizontal area of the plate 38 and the diameter of the holes 130 limit the addition of the other holes 130. The implant 10 with fenestrations 130 illustrated in FIG. 13 can be implanted in the anterior segment 34 of the eye 12 as described in association with FIGS. 10 and 11 above or in the posterior segment 35 of the eye 12 as described in association with FIGS. 8 and 9 above.

Although the invention has been described with reference to specific embodiments, the description is intended to be illustrative of the invention and is not intended to be limiting. Various modifications and applications may occur to those skilled in the art without departing from the true spirit and scope of the invention as defined in the appended claims.

What is claimed is:

1. A method of treating glaucoma in an eye utilizing an implant, said implant comprising a bleb formation device and an elastomeric drainage tube, wherein a first end of said elastomeric drainage tube is open to a surface of said bleb formation device, said method comprising the steps of:

positioning said bleb formation device in said eye, such that at least a portion of said bleb formation device is anterior to the location of muscle insertion of said eye;

forming a scar tissue bleb around said bleb formation device, such that at least a portion of said bleb is formed in the anterior segment of said eye;

positioning a second end of said drainage tube within the anterior chamber of said eye; and providing fluid communication between said anterior chamber and said scar tissue bleb.

2. A method of treating glaucoma as in claim 1, wherein said positioning step further comprises positioning said bleb formation device over the sclera of said eye.

3. A method of treating glaucoma as in claim 1, wherein said positioning step further comprises positioning said bleb formation device beneath Tenon's capsule of said eye.

4. A method of treating glaucoma as in claim 1, wherein the remainder of said bleb is formed in the anterior segment of said eye.

5. A method of treating glaucoma in an eye utilizing an implant, said implant comprising a bleb formation device and an elastomeric drainage tube, wherein a first end of said elastomeric drainage tube is open to a surface of said bleb formation device, said method comprising the steps of:

positioning said bleb formation device in said eye, such that at least a portion of said bleb formation device is anterior to the muscle insertions of the eye;

positioning a second end of said drainage tube within the anterior chamber of said eye; and providing fluid communication between said anterior chamber and a scar tissue bleb which forms around said implant.

6. A method of treating glaucoma as in claim 5, wherein said positioning step further comprises positioning said bleb formation device over the sclera of said eye.

7. A method of treating glaucoma as in claim 5, wherein said positioning step further comprises positioning said bleb formation device beneath Tenon's capsule of said eye.

8. A method of treating glaucoma as defined in claim 5, wherein said bleb formation device is an elastomeric plate.

9. A method of treating glaucoma as defined in claim 8, wherein said first end of said tube is open to a surface of said elastomeric plate.

10. A method of treating glaucoma as defined in claim 5, additionally comprising the step of suturing said bleb formation device to said eye.

11. A method of treating glaucoma as defined in claim 10, wherein said suturing step further comprises suturing said bleb formation device to the sclera of said eye.

12. A method of treating glaucoma in an eye utilizing an implant, said implant comprising a bleb formation device and an elastomeric drainage tube, wherein a first end of said elastomeric drainage tube is open to a surface of said bleb formation device, said method comprising the steps of:

positioning said bleb formation device over a sclera of said eye beneath Tenon's capsule, such that at least a portion of said bleb formation device is anterior to the muscle insertions of the eye;

positioning a second end of said drainage tube within the anterior chamber of said eye; and providing fluid communication between said anterior chamber and a scar tissue bleb which forms around said implant.

13. A method of treating glaucoma as defined in claim 12, wherein said positioning step further includes positioning said bleb formation device, such that between 5% and 99% of said bleb formation device is anterior to the muscle insertions of the eye.

14. A method of treating glaucoma as defined in claim 13, wherein said positioning step further includes positioning said bleb formation device, such that between 5% and 30% of said bleb formation device is anterior to the muscle insertions of the eye.

15. A method of treating glaucoma as defined in claim 12, wherein said bleb formation device is an elastomeric plate.

16. A method of treating glaucoma as defined in claim 12, additionally comprising the step of suturing said bleb formation device to said sclera.

17. A method of treating glaucoma in an eye utilizing an implant, said implant comprising an elastomeric bleb formation device and a drainage tube, wherein a first end of said drainage tube is open to a surface of said bleb formation device, said method comprising the steps of:

positioning said bleb formation device in said eye over the selera of said eye, and beneath Tenon's capsule of said eye, so that said bleb formation device elastomerically conforms to said eye, with at least a portion of said bleb formation device placed anterior to the muscle insertions of the eye, said positioning step including the acts of making an incision in said eye and passing said bleb formation device through said incision; and placing a second end of said drainage tube within the anterior chamber of said eye, said placing step comprising the acts of making a second incision into the anterior chamber of said eye and passing said second end of said drainage tube through said second incision into said anterior chamber of said eye.

18. A method of treating glaucoma as defined in claim 17 wherein said placing step further comprises the act of extending said second end of said drainage tube less than 10 mm from said bleb formation device.

19. A method of treating glaucoma as defined in claim 18 wherein said act of extending said second end of said drainage tube extends said second end less than 8 mm from said blab formation device.

20. A method of treating glaucoma in an eye utilizing an implant, said implant comprising an elastomeric bleb formation device and a drainage tube, wherein a first end of said drainage tube is open to a surface of said bleb formation device, said method comprising the steps of:

positioning said bleb formation device in said eye over the sclera of said eye, and beneath Tenon's capsule of said eye, so that said bleb formation device elastomerically conforms to said eye, said positioning step including the acts of making an incision in said eye and passing said bleb formation device through said incision; and placing a second end of said drainage tube within the anterior chamber of said eye less than 10 mm from said bleb formation device, said placing step comprising the acts of making a second incision into the anterior chamber of said eye and passing said second end of said drainage tube through said second incision into said anterior chamber of said eye.

21. A method of treating glaucoma as defined in claim 20 wherein said placing step places said second end of said drainage tube less than 8 mm from said bleb formation device.

* * * * *